(12) United States Patent
Boyd et al.

(10) Patent No.: US 7,851,471 B2
(45) Date of Patent: Dec. 14, 2010

(54) COMPOUNDS I

(75) Inventors: Joseph W. Boyd, Cambridgeshire (GB);
Giles A. Brown, Cambridge (GB);
Michael Higginbottom, Cambridgeshire (GB)

(73) Assignee: AstraZeneca AB (PUBL), Sodertalje (SE)

( * ) Notice: Subject to any disclaimer, the term of this patent is extended or adjusted under 35 U.S.C. 154(b) by 12 days.

(21) Appl. No.: 12/315,698

(22) Filed: Dec. 5, 2008

(65) Prior Publication Data
US 2009/0181967 A1 Jul. 16, 2009

Related U.S. Application Data

(60) Provisional application No. 61/022,983, filed on Jan. 23, 2008.

(30) Foreign Application Priority Data
Dec. 5, 2007 (SE) .................................. 0702696

(51) Int. Cl.
*A61K 31/535* (2006.01)
*A61K 31/497* (2006.01)
*C07D 413/00* (2006.01)
*C07D 405/00* (2006.01)
*C07D 409/00* (2006.01)
*C07D 411/00* (2006.01)

(52) U.S. Cl. ............... 514/235.8; 514/253.11; 544/121; 544/374

(58) Field of Classification Search .............. 514/235.8, 514/253.11; 544/121, 374
See application file for complete search history.

(56) References Cited

U.S. PATENT DOCUMENTS

| | | | |
|---|---|---|---|
| 2009/0176798 A1 | 7/2009 | Boyd et al. | |
| 2009/0203695 A1 | 8/2009 | Higginbottom et al. | |
| 2009/0281087 A1 | 11/2009 | Boyd et al. | |

FOREIGN PATENT DOCUMENTS

| EP | 0933361 | 8/1999 |
|---|---|---|
| EP | 1 787 679 | 5/2007 |
| JP | 2001-131149 | 5/2001 |
| JP | 2001-261657 | 9/2001 |
| WO | WO97/46585 | 12/1997 |
| WO | WO02/26723 | 4/2002 |
| WO | WO2005/016902 | 2/2005 |
| WO | WO2006/072393 | 7/2006 |
| WO | WO2007/022257 | 2/2007 |
| WO | WO2007/025613 | 3/2007 |
| WO | WO2007/098939 | 9/2007 |
| WO | WO2009/071668 | 6/2009 |
| WO | WO2009/147211 | 12/2009 |
| WO | WO2009/147216 | 12/2009 |
| WO | WO2009/147219 | 12/2009 |
| WO | WO2009/147221 | 12/2009 |

OTHER PUBLICATIONS

International Search Report dated Jun. 19, 2009 for International Appln. No. PCT/EP2008/066899 (International Publication No. W02009/071668), 2 pgs.
International-Type Search Report for Swedish Patent Appln. No. 0702697-4 dated Jun. 25, 2008, 8 pgs.
STN International Registry File, RN 913515-85-2 (Entry date Nov. 17, 2006), RN: 775282-94-5 (Entry date Nov. 5, 2006).
Banks, W.A. et al, *Brain Res.* (2002), 950:130-136.
Bouloumie A, et al, *Circ. Res.* (1998), 83-1059-1066.
Browning et al, *Metabolism* (2004), 53: 899-903.
Bryson, J.M., *Diabetes, Obesity and Metabolism* (2000), 2: 83-89.
Gonzalez et al, *Neuroendocrinology* (1999), 70: 213-220.
Gorden P, et al, *Current Opinion in Pharmacology* (2003), 3: 655-659.
Hanew, *Eur. J. Endocrin.* (2003), 149: 407-412.
Kastin, A.J., *Peptides* (1999), 20: 1449-1453.
Kinsella et al, *BMC Pharm* (2004), 4:17, 1-13.
Koistinen et al, *Eur. J. Clin. Invest.* (1998), 28: 894-897.
Lu et al, *Proc. Nat. Acad. Sci.*, (2006), 103: 1593-1598.
Lyon, C.J. et al, *Endocrinol.* (2003), 144: 2195-2200.
Maachi et al, *Int. J. Obes. Relat. Metab. Disord.* (2004), 28: 993-997.
Mangge et al, *Exp. Clin. Endocrinol. Diabetes* (2004), 112: 378-382.
Mantzoros, C.S., *Ann. Intern. Med.* (1999), 130-671-680.
Mirshamsi et al, *Regulatory Peptides* (2007), 141:19-24.
Mirshamsi et al, *J. Neuroendocrinology* (2005), 17, 246-254.
Otero, M. et al, *FEBS Lett* (2005), 579: 295-301.
Samson et al, *Endocrinol.* (1996), 137: 5182-5185.
Somasundar P. et al, *J. Surg. Res.* (2004), 116: 337-349.
Suganami E. et al, *Diabetes* (2004), 53: 2443-2448.
Van Heek et al, *J. Clin. Invest.* (1997), 99:385-390.
Zarkesh-Esfahani, H et al, *J. Immunol.* (2001), 167: 4593-4599.

Primary Examiner—San-ming Hui
Assistant Examiner—Paul Zarek
(74) Attorney, Agent, or Firm—Fish & Richardson P.C.

(57) ABSTRACT

The present application relates to new compounds of formula (I),

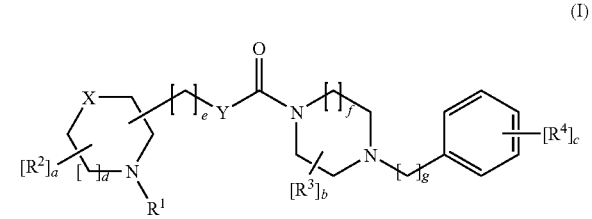

(I)

to pharmaceutical compositions comprising the compounds, to processes for their preparation, and to the use of the compounds as leptin receptor modulator mimetics in the preparation of medicaments against conditions associated with weight gain, type 2 diabetes and dyslipidemias.

20 Claims, 5 Drawing Sheets

COMPOUNDS I

CROSS-REFERENCE TO RELATED APPLICATIONS

This application claims the benefit of Swedish Application No. 0702696-6, filed Dec. 5, 2007 and of U.S. Provisional Application No. 61/022,983, filed Jan. 23, 2008, the entire disclosures of which are hereby incorporated by reference in their entireties.

FIELD OF THE INVENTION

The present application relates to new piperazine derivatives, to pharmaceutical compositions comprising the compounds, to processes for their preparation, and to the use of the compounds as leptin receptor modulator mimetics in the preparation of medicaments against conditions associated with weight gain, type 2 diabetes and dyslipidemias.

BACKGROUND ART

The prevalence of obesity is increasing in the industrialized world. Typically, the first line of treatment is to offer diet and life style advice to patients, such as reducing the fat content of their diet and increasing their physical activity. However, some patients may also need to undergo drug therapy to maintain the beneficial results obtained from adapting the aforementioned diet and lifestyle changes.

Leptin is a hormone synthesized in fat cells that is believed to act in the hypothalamus to reduce food intake and body weight (see, e.g., Bryson, J. M. (2000) Diabetes, Obesity and Metabolism 2: 83-89).

It has been shown that in obese humans the ratio of leptin in the cerebrospinal fluid to that of circulating leptin is decreased (Koistinen et al., (1998) Eur. J. Clin. Invest. 28: 894-897). This suggests that the capacity for leptin transport into the brain is deficient in the obese state. Indeed, in animal models of obesity (NZO mouse and Koletsky rat), defects in leptin transport have been shown to result in reduced brain leptin content (Kastin, A. J. (1999) Peptides 20: 1449-1453; Banks, W. A. et al., (2002) Brain Res. 950: 130-136). In studies involving dietary-induced obese rodents (a rodent model that is believed to more closely resemble human obesity, see, e.g., Van Heek et al. (1997) J. Clin. Invest. 99: 385-390), excess leptin administered peripherally was shown to be ineffective in reducing food intake and body weight, whereas leptin injected directly into the brain was effective in reducing food intake and body weight. It has also been shown that in obese humans with excess circulating leptin, the signaling system became desensitized to the continual stimulation of the leptin receptors (Mantzoros, C. S. (1999) Ann. Intern. Med. 130: 671-680).

Amgen has conducted clinical trials with recombinant methionyl human leptin. The results from these trials were mixed, as even in the presence of high plasma concentrations of leptin weight loss was variable, and the average weight reduction in the cohort of patients tested relatively small (Obesity Strategic Perspective, Datamonitor, 2001).

Several attempts at finding active fragments have been reported in the literature since the discovery of the leptin gene coding sequence. An example is by Samson et al. (1996) Endocrinol. 137: 5182-5185 which describes an active fragment at the N-terminal (22 to 56). This sequence was shown to reduce food intake when injected ICV whereas a sequence taken at the C-terminal was shown not to have any effect. Leptin fragments are also disclosed in International Patent Application WO 97/46585.

Other reports looking at the C-terminus part of the sequence reported a possible stimulation of luteinising hormone production by a 116-130 fragment (Gonzalez et al., (1999) Neuroendocrinology 70:213-220) and an effect on GH production following GHRH administration (fragment 126-140) (Hanew (2003) Eur. J. Endocrin. 149: 407-412).

Leptin has recently been associated with inflammation. It has been reported that circulating leptin levels rise during bacterial infection and in inflammation (see Otero, M et al. (2005) FEBS Lett. 579: 295-301 and references therein). Leptin can also act to increase inflammation by enhancing the release of pro-inflammatory cytokines TNF and IL-6 from inflammatory cells (Zarkesh-Esfahani, H. et al. (2001) J. Immunol. 167: 4593-4599). These agents in turn can contribute to the insulin resistance commonly seen in obese patients by reducing the efficacy of insulin receptor signaling (Lyon, C. J. et al. (2003) Endocrinol. 44: 2195-2200). Continuous low grade inflammation is believed to be associated with obesity (in the presence and absence of insulin resistance and Type II diabetes) (Browning et al. (2004) Metabolism 53: 899-903, Inflammatory markers elevated in blood of obese women; Mangge et al. (2004) Exp. Clin. Endocrinol. Diabetes 112: 378-382, Juvenile obesity correlates with serum inflammatory marker C-reactive protein; Maachi et al. (2004) Int. J. Obes. Relat. Metab. Disord. 28: 993-997, Systemic low grade inflammation in obese people). Leptin has also been implicated in the process of atherogenesis, by promoting lipid uptake into macrophages and endothelial dysfunction, thus promoting the formation of atherosclerotic plaques (see Lyon, C. J. et al. (2003) Endocrinol. 144: 2195-2200).

Leptin has also been shown to promote the formation of new blood vessels (angiogenesis) a process implicated in the growth of adipose tissue (Bouloumie A, et al. (1998) Circ. Res. 83: 1059-1066). Angiogenesis has also been implicated in diabetic retinopathy (Suganami, E. et al. (2004) Diabetes. 53: 2443-2448).

Angiogenesis is also believed to be involved with the growth of new blood vessels that feed abnormal tumour cells. Elevated leptin levels have been associated with a number of cancers, in particular breast, prostate and gastrointestinal cancers in humans (Somasundar P. et al. (2004) J. Surg. Res. 116: 337-349).

Leptin receptor agonists may also be used in the manufacture of a medicament to promote wound healing (Gorden, P. and Gavrilova, O. (2003) Current Opinion in Pharmacology 3: 655-659).

Further, it has been shown that elevating leptin signaling in the brain may represent an approach for the treatment of depressive disorders (Lu, Xin-Yun et al. (2006) PNAS 103: 1593-1598).

DISCLOSURE OF THE INVENTION

It has surprisingly been found that compounds of formula (I) are effective in reducing body weight and food intake in rodents. While not wishing to be bound by theory, it is proposed that the compounds of formula I modulate the leptin receptor signaling pathway.

In some embodiments, compounds with leptin receptor agonistic like properties can be useful for the treatment of disorders relating to leptin signaling, as well as conditions associated with weight gain, such as obesity. The inventors hypothesized that small molecule CNS penetrant leptin mimetics would be able to by-pass the limiting uptake system into the brain. Further, assuming that this situation mirrors the human obese condition, the inventors believe that a CNS-active leptinoid with a relatively long duration of action would make an effective therapy for the obese state and its attendant complications, in particular (but not limited to) diabetes.

In other embodiments, compounds with leptin receptor antagonistic like properties could be useful for the treatment of inflammation, atherosclerosis, diabetic retinopathy and nephropathy.

In a first aspect, the disclosure relates to a compound of formula (I),

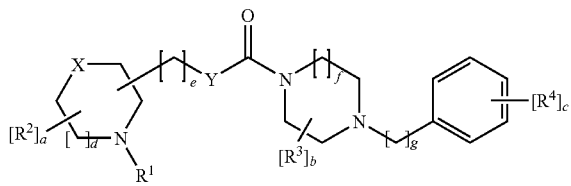

(I)

and pharmaceutically acceptable salts, hydrates, geometrical isomers, racemates, tautomers, optical isomers or N-oxides thereof, wherein:

X is selected from O, S, N($R^1$) and CH($R^2$), provided that the ring containing X is not 3-pyrrolidine;

Y is $CH_2$, O or N($R^5$);

$R^1$ is independently selected from hydrogen, $C_{1-6}$-alkyl (unsubstituted or optionally substituted with one or more substituents independently selected from halogen, hydroxy, cyano and $C_{1-6}$-alkoxy) and $C_{1-6}$-acyl (unsubstituted or optionally substituted with one or more substituents independently selected from halogen, hydroxy and $C_{1-6}$-alkoxy);

$R^1$ and $R^3$ are independently selected from hydrogen, halogen, hydroxy, $C_{1-6}$-alkyl (unsubstituted or optionally substituted with one or more substituents independently selected from halogen, hydroxy and $C_{1-6}$-alkoxy) and $C_{1-6}$-alkoxy (unsubstituted or optionally substituted with one or more substituents independently selected from halogen, hydroxy and $C_{1-6}$-alkoxy);

$R^4$ is independently selected from hydrogen, halogen, hydroxy, cyano, nitro, $CF_3$, $C_{1-6}$-alkyl and $C_{1-6}$-alkoxy;

$R^5$ is hydrogen or $C_{1-4}$-alkyl;

a, b and c are each independently 1, 2 or 3;

d is 0, 1 or 2;

e is 1, 2 or 3; and f and g are each independently 0, 1 or 2.

In a preferred embodiment, Y is O.

In another embodiment, X is preferably selected from O, N($R^1$) and CH($R^2$).

$R^1$ is preferably selected from hydrogen, $C_{1-4}$-alkyl and $C_{1-4}$-acyl.

In a most preferred embodiment, $R^1$ is hydrogen, methyl or acetyl.

$R^2$ and $R^3$ are preferably independently selected from hydrogen and $C_{1-4}$-alkyl.

In a most preferred embodiment, $R^2$ and $R^3$ are hydrogen.

$R^4$ is preferably independently selected from hydrogen, halogen, $CF_3$ and $C_{1-4}$-alkyl.

In a most preferred embodiment, $R^4$ is independently selected from hydrogen, fluoro, chloro or methyl.

d and f are each preferably 1.

e is preferably 1 or 2.

g is preferably 0 or 1, and more preferably 0.

Particular preferred compounds of formula (I) are the compounds of formula (I')

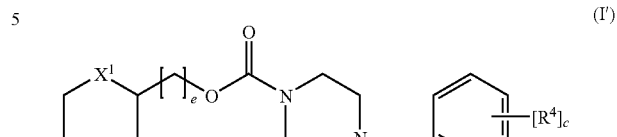

(I')

wherein:

$X^1$ and $X^2$ are each independently selected from O, N($R^1$) or CH($R^2$), provided that at least one of $X^1$ and $X^2$ is N($R^1$);

$R^1$ is as defined in formula (I), and preferably hydrogen, methyl or acetyl;

$R^2$ is as defined in formula (I), and preferably hydrogen;

$R^4$ is hydrogen, fluoro, chloro or methyl;

c is 1, 2 or 3;

e is 1 or 2; and g is 0 or 1.

Specific preferred compounds of formula (I) are those selected from the group consisting of:

[(3R)-1-methylpiperidin-3-yl]methyl 4-(4-methylphenyl)piperazine-1-carboxylate;

[(3S)-1-methylpiperidin-3-yl]methyl 4-(4-methylphenyl)piperazine-1-carboxylate;

[(2S)-1,4-dimethylpiperazin-2-yl]methyl 4-phenylpiperazine-1-carboxylate;

[(2R)-1,4-dimethylpiperazin-2-yl]methyl 4-phenylpiperazine-1-carboxylate;

[(2S)-1,4-dimethylpiperazin-2-yl]methyl 4-(4-fluorophenyl)piperazine-1-carboxylate;

[(2R)-1,4-dimethylpiperazin-2-yl]methyl 4-(4-fluorophenyl)piperazine-1-carboxylate;

4-phenylpiperazine-1-carboxylic acid 2-(1,4-dimethylpiperazin-2-yl)ethyl ester;

[(2S)-1,4-dimethylpiperazin-2-yl]methyl 4-(2,4-difluorophenyl)piperazine-1-carboxylate;

[(2S)-4-methylpiperazin-2-yl]methyl 4-phenylpiperazine-1-carboxylate;

(1,4-dimethylpiperazin-2-yl)methyl 4-benzylpiperazine-1-carboxylate;

morpholin-2-ylmethyl 4-phenylpiperazine-1-carboxylate;

(2S)-morpholin-2-ylmethyl 4-phenylpiperazine-1-carboxylate;

(2R)-morpholin-2-ylmethyl 4-phenylpiperazine-1-carboxylate;

(4-methylmorpholin-2-yl)methyl 4-phenylpiperazine-1-carboxylate;

[(2S)-4-methylmorpholin-2-yl]methyl 4-phenylpiperazine-1-carboxylate;

[(2R)-4-methylmorpholin-2-yl]methyl 4-phenylpiperazine-1-carboxylate;

[(2S)-4-methylmorpholin-2-yl]methyl 4-(4-fluorophenyl)piperazine-1-carboxylate;

[(2R)-4-methylmorpholin-2-yl]methyl 4-(4-fluorophenyl)piperazine-1-carboxylate;

[(2S)-4-methylmorpholin-2-yl]methyl 4-(2,4-difluorophenyl)piperazine-1-carboxylate;

[(2R)-4-methylmorpholin-2-yl]methyl 4-(2,4-difluorophenyl)piperazine-1-carboxylate;

morpholin-2-ylmethyl 4-(4-fluorophenyl)piperazine-1-carboxylate;

(2S)-morpholin-2-ylmethyl 4-(4-fluorophenyl)piperazine-1-carboxylate;
(2R)-morpholin-2-ylmethyl 4-(4-fluorophenyl)piperazine-1-carboxylate;
(4-methylmorpholin-2-yl)methyl 4-(4-chlorophenyl)piperazine-1-carboxylate;
(4-methylmorpholin-2-yl)methyl 4-(4-fluorobenzyl)piperazine-1-carboxylate;
(4-acetylmorpholin-2-yl)methyl 4-phenylpiperazine-1-carboxylate;
morpholin-3-ylmethyl 4-(4-fluorophenyl)piperazine-1-carboxylate;
(3S)-morpholin-3-ylmethyl 4-(4-fluorophenyl)piperazine-1-carboxylate;
(3R)-morpholin-3-ylmethyl 4-(4-fluorophenyl)piperazine-1-carboxylate;
(4-methylmorpholin-3-yl)methyl 4-(4-fluorophenyl)piperazine-1-carboxylate;
morpholin-3-ylmethyl 4-phenylpiperazine-1-carboxylate;
morpholin-3-ylmethyl 4-(2,4-difluorophenyl)piperazine-1-carboxylate;
(4-methylmorpholin-3-yl)methyl 4-(2,4-difluorophenyl)piperazine-1-carboxylate;
(2S)-morpholin-2-ylmethyl 4-(2,4-difluorophenyl)piperazine-1-carboxylate; and
(2R)-morpholin-2-ylmethyl 4-(2,4-difluorophenyl)piperazine-1-carboxylate.

Another aspect of the present disclosure is a compound of formula (I) for use in therapy.

In a further aspect, the disclosure relates to a compound of formula (I) for use in the treatment or prevention of any of the disorders or conditions described herein.

In yet a further aspect, the invention relates to the use of a compound of formula (I) in the manufacture of a medicament for the treatment or prevention of any of the disorders or conditions described herein.

In some embodiments, said compounds may be used in the manufacture of a medicament for the treatment or prevention of a condition that is prevented, treated, or ameliorated by selective action on the leptin receptor.

In some embodiments, said compounds may be used in the manufacture of a medicament for the treatment or prevention of conditions (in particular, metabolic conditions) that are associated with weight gain. Conditions associated with weight gain include diseases, disorders, or other conditions that have an increased incidence in obese or overweight subjects. Examples include: lipodystrophy, HIV lipodystrophy, diabetes (type 2), insulin resistance, metabolic syndrome, hyperglycemia, hyperinsulinemia, dyslipidemia, hepatic steatosis, hyperphagia, hypertension, hypertriglyceridemia, infertility, a skin disorder associated with weight gain, macular degeneration. In some embodiments, the compounds may also be used in the manufacture of a medicament for maintaining weight loss of a subject.

In some embodiments, compounds of formula (I) which are leptin receptor agonist mimetics may also be used in the manufacture of a medicament to promote wound healing.

In some embodiments, compounds of formula (I) which are leptin receptor agonist mimetics may also be used in the manufacture of a medicament for the treatment or prevention of conditions that cause a decrease in circulating leptin concentrations, and the consequent malfunction of the immune and reproductive systems. Examples of such conditions and malfunctions include severe weight loss, dysmenorrhea, amenorrhea, female infertility, immunodeficiency and conditions associated with low testosterone levels.

In some embodiments, compounds of formula (I) which are leptin receptor agonist mimetics may also be used in the manufacture of a medicament for the treatment or prevention of conditions caused as a result of leptin deficiency, or a leptin or leptin receptor mutation.

In some other embodiments, compounds of formula (I) which are leptin receptor antagonist mimetics may be used for the treatment or prevention of inflammatory conditions or diseases, low level inflammation associated with obesity and excess plasma leptin and in reducing other complications associated with obesity including atherosclerosis, and for the correction of insulin resistance seen in Metabolic Syndrome and diabetes.

In some embodiments, compounds of formula (I) which are leptin receptor antagonist mimetics can be used for the treatment or prevention of inflammation caused by or associated with: cancer (such as leukemias, lymphomas, carcinomas, colon cancer, breast cancer, lung cancer, pancreatic cancer, hepatocellular carcinoma, kidney cancer, melanoma, hepatic, lung, breast, and prostate metastases, etc.); autoimmune disease (such as organ transplant rejection, lupus erythematosus, graft v. host rejection, allograft rejections, multiple sclerosis, rheumatoid arthritis, type I diabetes mellitus including the destruction of pancreatic islets leading to diabetes and the inflammatory consequences of diabetes); autoimmune damage (including multiple sclerosis, Guillam Barre Syndrome, myasthenia gravis); cardiovascular conditions associated with poor tissue perfusion and inflammation (such as atheromas, atherosclerosis, stroke, ischaemia-reperfusion injury, claudication, spinal cord injury, congestive heart failure, vasculitis, haemorrhagic shock, vasospasm following subarachnoid haemorrhage, vasospasm following cerebrovascular accident, pleuritis, pericarditis, the cardiovascular complications of diabetes); ischaemia-reperfusion injury, ischaemia and associated inflammation, restenosis following angioplasty and inflammatory aneurysms; epilepsy, neurodegeneration (including Alzheimer's Disease), arthritis (such as rheumatoid arthritis, osteoarthritis, rheumatoid spondylitis, gouty arthritis), fibrosis (for example of the lung, skin and liver), multiple sclerosis, sepsis, septic shock, encephalitis, infectious arthritis, Jarisch-Herxheimer reaction, shingles, toxic shock, cerebral malaria, Lyme's disease, endotoxic shock, gram negative shock, haemorrhagic shock, hepatitis (arising both from tissue damage or viral infection), deep vein thrombosis, gout; conditions associated with breathing difficulties (e.g. chronic obstructive pulmonary disease, impeded and obstructed airways, bronchoconstriction, pulmonary vasoconstriction, impeded respiration, chronic pulmonary inflammatory disease, silicosis, pulmonary sarcosis, cystic fibrosis, pulmonary hypertension, pulmonary vasoconstriction, emphysema, bronchial allergy and/or inflammation, asthma, hay fever, rhinitis, vernal conjunctivitis and adult respiratory distress syndrome); conditions associated with inflammation of the skin (including psoriasis, eczema, ulcers, contact dermatitis); conditions associated with inflammation of the bowel (including Crohn's disease, ulcerative colitis and pyresis, irritable bowel syndrome, inflammatory bowel disease); HIV (particularly HIV infection), cerebral malaria, bacterial meningitis, osteoporosis and other bone resorption diseases, osteoarthritis, infertility from endometriosis, fever and myalgia due to infection, and other conditions mediated by excessive anti-inflammatory cell (including neutrophil, eosinophil, macrophage and T-cell) activity.

In some embodiments, compounds of formula (I) which are leptin receptor antagonists mimetics may be used for the treatment or prevention of macro or micro vascular complications of type 1 or 2 diabetes, retinopathy, nephropathy, autonomic neuropathy, or blood vessel damage caused by ischaemia or atherosclerosis.

In some embodiments, compounds of formula (I) which are leptin receptor antagonist mimetics may be used to inhibit angiogenesis. Compounds that inhibit angiogenesis may be used for the treatment or prevention of obesity or complications associated with obesity. Compounds that inhibit angiogenesis may be used for the treatment or prevention of complications associated with inflammation diabetic retinopathy, or tumour growth particularly in breast, prostate or gastrointestinal cancer.

In a further aspect, the disclosure relates to a method for the treatment or prevention of any of the disorders or conditions described herein, which includes administering to a subject (e.g., a subject in need thereof, e.g., a mammal) an effective amount of a compound of formula I.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the disclosure provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this disclosure; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the disclosure is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radio-labeling/assay techniques, blotting/chemiluminescence methods, real-time PCR, and the like.

In some embodiments, it may be advantageous if a compound of formula (I) is able to penetrate the central nervous system. In other embodiments, it may be advantageous if a compound of formula (I) is not able to penetrate the CNS. In general, it is expected that compounds that are leptin receptor agonist mimetics may be particularly useful for the treatment or prevention of obesity, insulin resistance, or diabetes (particularly glucose intolerance) if these compounds can penetrate the CNS. A person of ordinary skill in the art can readily determine whether a compound can penetrate the CNS. A suitable method that may be used is described in the Biological Methods section.

A leptin receptor response may be measured in any suitable way. In vitro, this may be done be measuring leptin receptor signaling. For example, phosphorylation of Akt, STAT3, STAT5, MAPK, shp2 or the leptin receptor in response to binding of leptin or a compound of the disclosure to the leptin receptor may be measured. The extent of phosphorylation of Akt, STAT3, STAT5, MAPK, shp2 or the leptin receptor may be determined for example by Western blotting or by ELISA. Alternatively, a STAT reporter assay may be used, for example STAT driven luciferase expression. A cell line expressing the leptin receptor may be used for such assays. In vivo, leptin receptor response may be measured by determining the reduction in food intake and body weight after administration of leptin or a compound of the disclosure.

The Biological Methods below describe assays and methods that can be used to determine whether a compound of the disclosure is a leptin receptor agonist mimetic or a leptin receptor antagonist mimetic.

A compound of formula (I) may be administered with or without other therapeutic agents. For example, where it is desired to reduce inflammation, the compound may be administered with an anti-inflammatory agent (for example, disease modifying anti-rheumatic drugs such as methotrexate, sulphasalazine and cytokine inactivating agents, steroids, NSAIDs, cannabinoids, tachykinin modulators, or bradykinin modulators). Where it is desired to provide an anti-tumour effect, a compound of formula (I) may be administered with a cytotoxic agent (for example, methotrexate, cyclophosphamide) or another anti-tumour drug.

Compounds of formula (I) may be radiolabeled (for example with tritium or radioactive iodine) for in vitro or in vivo applications, such as receptor displacement studies or receptor imaging.

A further aspect of the present disclosure relates to processes for the manufacture of compounds of formula (I) as defined above. In one embodiment, the process comprises:

(a) reacting a compound of formula (II):

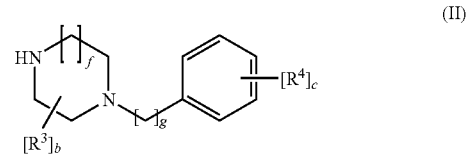

(II)

wherein $R^3$, $R^4$, b, c, f and g are as defined in formula (I), with 4-nitrophenyl chloroformate or bis-(4-nitrophenyl)carbonate in the presence of a suitable base (such as DIPEA or NEt₃) in a suitable solvent (such as DCM or THF), at −10 to 40° C., to form a compound of formula (III):

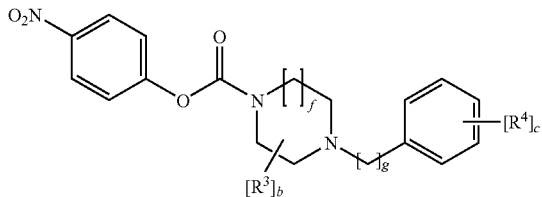

(III)

(b) reacting the compound of formula (III) with a compound of formula (IV):

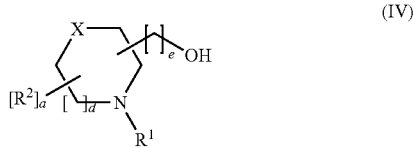

(IV)

wherein X, R¹, R², a, d and e are as defined in formula (I), in the presence of a suitable base, (such as NaH or NMM), in a suitable solvent (such as THF or DCM), at −10 to 40° C., to obtain a compound of formula (I); and (c) optionally, in one or several steps transforming a compound of formula (I) into another compound of formula (I).

In another embodiment, the process comprises:

(a) reacting a compound of formula (IV):

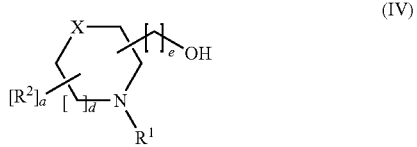

(IV)

wherein X, R¹, R², a, d and e are as defined in formula (I), with 4-nitrophenyl chloroformate or bis-(4-nitrophenyl)carbonate in the presence of a suitable base (such as DIPEA or NMM) in a suitable solvent (such as DCM), at −10 to 40° C., to form a compound of formula (V):

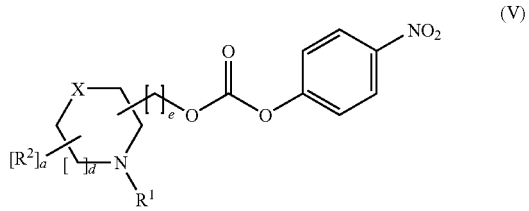

(V)

(b) reacting the compound of formula (V) with a compound of formula (II):

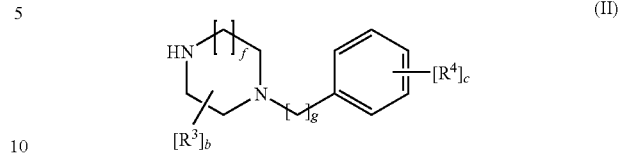

(II)

wherein R³, R⁴, b, c, f and g are as defined in formula (I), in the presence of a suitable base, (such as DIPEA), in a suitable solvent (such as DCM or DMF), at −10 to 40° C., to obtain a compound of formula (I); and (c) optionally, in one or several steps transforming a compound of formula (I) into another compound of formula (I).

DEFINITIONS

The following definitions shall apply throughout the specification and the appended claims.

Unless otherwise stated or indicated, the term "$C_{1-6}$-alkyl" denotes a straight or branched alkyl group having from 1 to 6 carbon atoms. Examples of said $C_{1-6}$-alkyl include methyl, ethyl, n-propyl, iso-propyl, n-butyl, iso-butyl, sec-butyl, t-butyl, and straight- and branched-chain pentyl and hexyl. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc.

Unless otherwise stated or indicated, the term "$C_{1-6}$-acyl" denotes a carbonyl group that is attached through its carbon atom to a hydrogen atom (i.e., a formyl group) or to a straight or branched $C_{1-5}$-alkyl group, where alkyl is defined as above. Examples of said $C_{1-6}$-acyl include formyl, acetyl, propionyl, n-butyryl, 2-methylpropionyl and n-pentoyl. For parts of the range "$C_{1-6}$-acyl" all subgroups thereof are contemplated such as $C_{1-5}$-acyl, $C_{1-4}$-acyl, $C_{1-3}$-acyl, $C_{1-2}$-acyl, $C_{2-6}$-acyl, $C_{2-5}$-acyl, $C_{2-4}$-acyl, $C_{2-3}$-acyl, $C_{3-6}$-acyl, $C_{4-5}$-acyl, etc. If a $C_{1-6}$-acyl group is optionally substituted with one or more substituents independently selected from halogen, hydroxy and $C_{1-6}$-alkoxy, said substituent can not be attached to the carbonyl carbon atom.

Unless otherwise stated or indicated, the term "$C_{1-6}$-alkoxy" denotes a straight or branched alkoxy group having from 1 to 6 carbon atoms. Examples of said $C_{1-6}$-alkoxy include methoxy, ethoxy, n-propoxy, iso-propoxy, n-butoxy, iso-butoxy, sec-butoxy, t-butoxy, and straight- and branched-chain pentoxy and hexoxy. For parts of the range "$C_{1-6}$-alkoxy" all subgroups thereof are contemplated such as $C_{1-5}$-alkoxy, $C_{1-4}$-alkoxy, $C_{1-3}$-alkoxy, $C_{1-2}$-alkoxy, $C_{2-6}$-alkoxy, $C_{2-5}$-alkoxy, $C_{2-4}$-alkoxy, $C_{2-3}$-alkoxy, $C_{3-6}$-alkoxy, $C_{4-5}$-alkoxy, etc.

"Halogen" refers to fluorine, chlorine, bromine or iodine.

"Hydroxy" refers to the —OH radical.

"Nitro" refers to the —NO₂ radical.

"Cyano" refers to the —CN radical.

"Optional" or "optionally" means that the subsequently described event or circumstance may but need not occur, and that the description includes instances where the event or circumstance occurs and instances in which it does not.

The term "mammal" includes organisms, which include mice, rats, cows, sheep, pigs, rabbits, goats, and horses, monkeys, dogs, cats, and preferably humans. The subject may be a human subject or a non human animal, particularly a domesticated animal, such as a dog. "Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect (e.g., treats, controls, ameliorates, prevents, delays the onset of, or reduces the risk of developing a disease, disorder, or condition or symptoms thereof) on the treated subject. The therapeutic effect may be objective (i.e., measurable by some test or marker) or subjective (i.e., subject gives an indication of or feels an effect).

"Prodrugs" refers to compounds that may be converted under physiological conditions or by solvolysis to a biologically active compound of formula (I). A prodrug may be inactive when administered to a subject in need thereof, but is converted in vivo to an active compound of formula (I). Prodrugs are typically rapidly transformed in vivo to yield the parent compound, e.g. by hydrolysis in the blood. The prodrug compound usually offers advantages of solubility, tissue compatibility or delayed release in a mammalian organism (see Silverman, R. B., *The Organic Chemistry of Drug Design and Drug Action, 2$^{nd}$* Ed., Elsevier Academic Press (2004), pp. 498-549). Prodrugs may be prepared by modifying functional groups, such as a hydroxy, amino or mercapto groups, present in a compound of formula (I) in such a way that the modifications are cleaved, either in routine manipulation or in vivo, to the parent compound. Examples of prodrugs include, but are not limited to, acetate, formate and succinate derivatives of hydroxy functional groups or phenyl carbamate derivatives of amino functional groups.

Throughout the specification and the appended claims, a given chemical formula or name shall also encompass all hydrates and solvates thereof. Further, a given chemical formula or name shall encompass all tautomeric and stereoisomeric forms thereof. Stereoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometrical isomers, which can be present in their pure cis or trans forms or as mixtures of those.

The compounds of formula (I) may be used as such or, where appropriate, as pharmacologically acceptable salts (acid or base addition salts) thereof. The pharmacologically acceptable addition salts mentioned below are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

Compositions

For clinical use, the compounds of the disclosure are formulated into pharmaceutical formulations for various modes of administration. It will be appreciated that the compounds may be administered together with a physiologically acceptable carrier, excipient, or diluent. The pharmaceutical compositions may be administered by any suitable route, preferably by oral, rectal, nasal, topical (including buccal and sublingual), sublingual, transdermal, intrathecal, transmucosal or parenteral (including subcutaneous, intramuscular, intravenous and intradermal) administration.

Other formulations may conveniently be presented in unit dosage form, e.g., tablets and sustained release capsules, and in liposomes, and may be prepared by any methods well known in the art of pharmacy. Pharmaceutical formulations are usually prepared by mixing the active substance, or a pharmaceutically acceptable salt thereof, with conventional pharmaceutically acceptable carriers, diluents or excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner. To maintain therapeutically effective plasma concentrations for extended periods of time, compounds of the disclosure may be incorporated into slow release formulations.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

Preparation of Compounds of the Invention

The compounds of formula (I) above may be prepared by, or in analogy with, conventional methods. Formation of the central urethane or urea linker is the key synthetic step in preparing the compounds formula (I). A large number of activating reagents can be used for the formation of a urethane or urea linker e.g. phosgene to form chloroformate of alcohols, or carbonyldiimidazole (CDI) to form imidazole carboxylates. Typically the urethane linkers incorporated into compounds of formula (I) have been synthesized utilizing 4-nitrophenyl chloroformate or bis-(4-nitrophenyl)carbonate as the activating agent. The preparation of intermediates and compounds according to the examples of the present disclosure may in particular be illuminated by the following Schemes 1 and 2. Definitions of variables in the structures in the schemes herein are commensurate with those of corresponding positions in the formulae delineated herein.

Scheme 1. Preparation by activation of the piperazine moiety

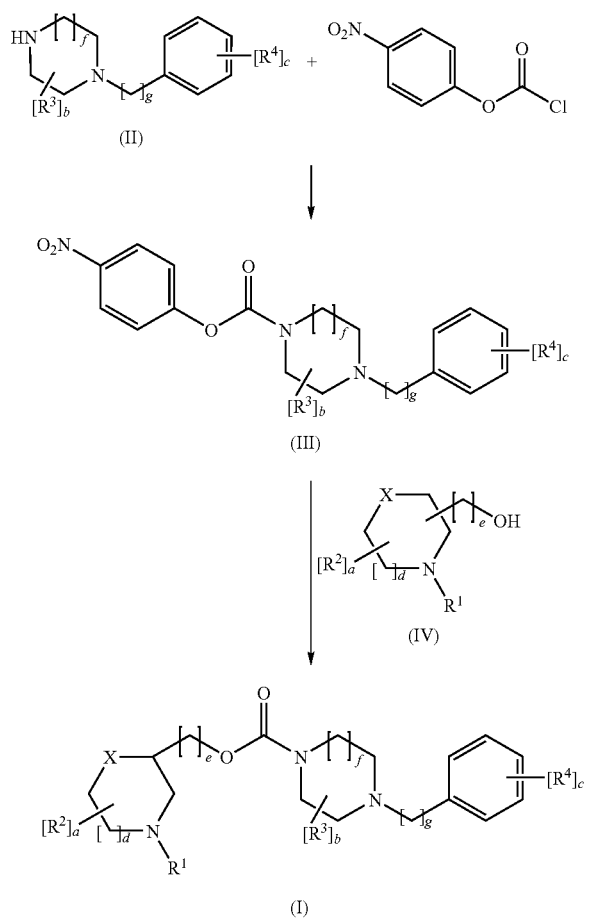

wherein X, $R^1$-$R^4$ and a-g are as defined in formula 1.

In one procedure, as generally represented in Scheme 1, the piperazine moiety is activated by treating piperazine derivative (II) with 4-nitrophenyl chloroformate or bis-(4-nitrophenyl)carbonate in the presence of a base (such as DIPEA) to form the corresponding carbamate derivative (III). Treatment of this activated intermediate with the appropriate alcohol moiety (IV) in the presence of a base (such as NaH) results in the formation of the desired compound of formula (I).

Scheme 2. Preparation by activation of the alcohol moiety

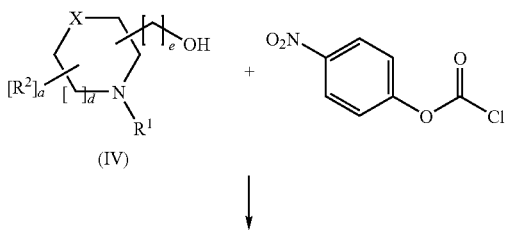

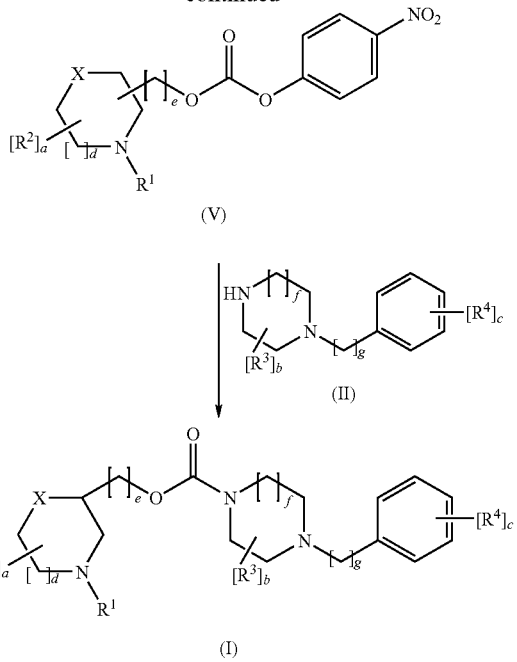

wherein X, $R^1$-$R^4$ and a-g are as defined in formula 1.

In an alternative procedure, the alcohol moiety is activated by treating alcohol (IV) with 4-nitrophenyl chloroformate or bis-(4-nitrophenyl)carbonate in the presence of a base (such as DIPEA) to form the corresponding 4-nitrophenyl carbonate derivative (V). In the next step, the activated carbonate (V) is treated with the appropriate piperazine moiety (II) in the presence of a base (such as DIPEA), resulting in the formation of the desired compound of formula (I). This is generally represented in Scheme 2.

The formation of the urethane is typically a two step process but this may also be performed in a one-pot reaction by formation of the activated intermediate in situ. The experimental section below gives examples of all of these synthetic alternatives.

The necessary starting materials for preparing the compounds of formula (I) are either commercially available, or may be prepared by methods known in the art.

The processes described below in the experimental section may be carried out to give a compound in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are mentioned above.

The compounds of formula (I) may possess one or more chiral carbon atoms, and they may therefore be obtained in the form of optical isomers, e.g., as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes delineated herein may include, for example, solvents, reagents, catalysts, and protecting group and deprotecting group reagents. Examples of protecting groups are t-butoxycarbonyl (Boc), benzyl and trityl (triphenylmethyl). The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The following abbreviations have been used:
t-AmOH tert-Amylalcohol
Boc tert-Butoxycarbonyl
t-Bu tert-Butyl
DCM Dichloromethane
DIPEA N,N-Diisopropylethylamine
DMF N,N-Dimethylformamide
ES$^+$ Electrospray
Et$_2$O Diethyl ether
EtOAc Ethyl acetate
HIV Human immunodeficiency virus
HPLC High performance liquid chromatography
ICV Intracerebroventricular
LCMS Liquid Chromatography Mass Spectrometry
M Molar
[MH]$^+$ Protonated molecular ion
NEt$_3$ Triethylamine
NMM N-methyl morpholine
RP Reverse Phase
tert Tertiary
TFA Trifluoroacetic acid
THF Tetrahydrofuran Embodiments of the disclosure are described in the following examples with reference to the accompanying drawings, in which:

Figure 1:
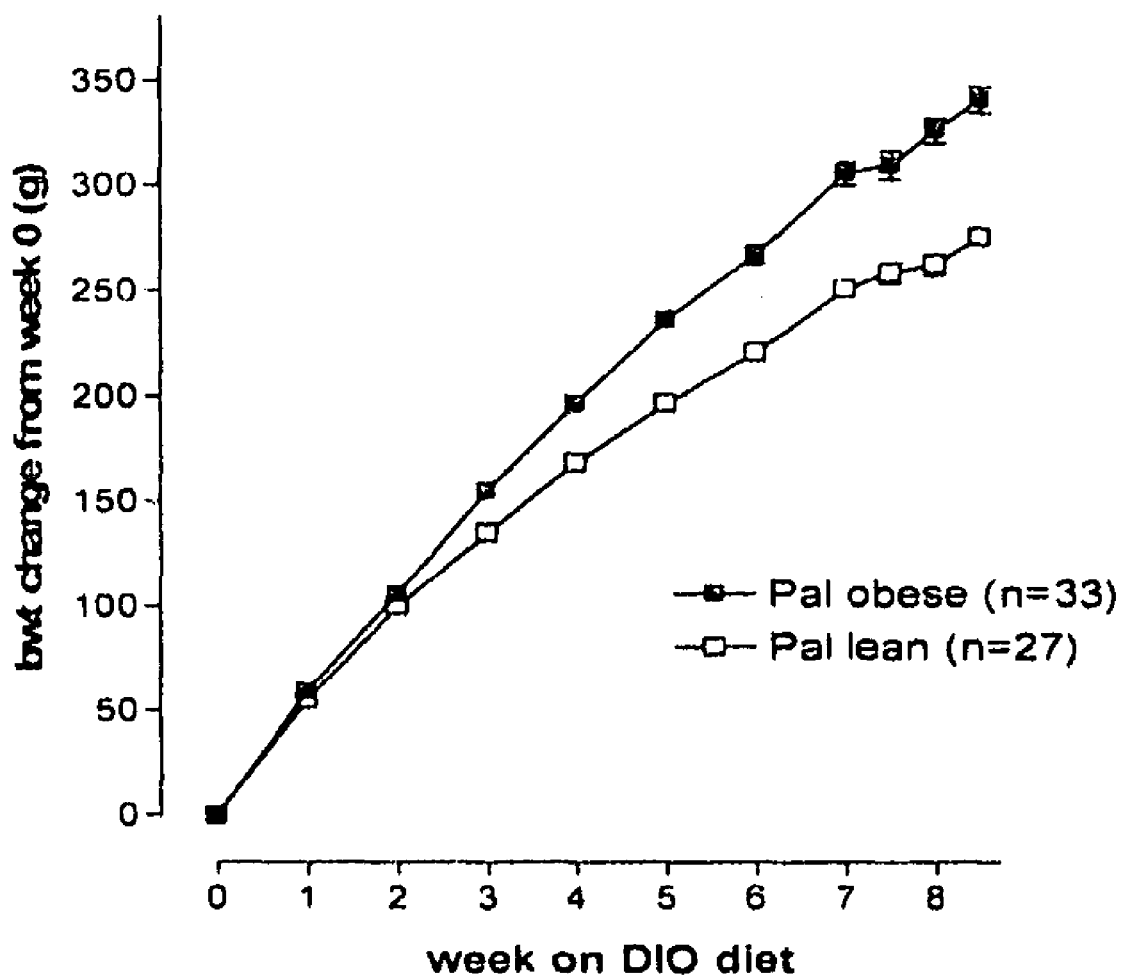
FIG. 1 shows an example of body weight separation between animals fed on a high carbohydrate diet. The error bars represent mean+/−SEM.

The recitation of a listing of chemical groups in any definition of a variable herein includes definitions of that variable as any single group or combination of listed groups. The recitation of an embodiment herein includes that embodiment as any single embodiment or in combination with any other embodiments or portions thereof.

The disclosure will now be further illustrated by the following non-limiting examples. The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All references and publications cited herein are hereby incorporated by reference in their entirety.

EXAMPLES AND INTERMEDIATE COMPOUNDS

Experimental Methods

All reagents were commercial grade and were used as received without further purification, unless otherwise specified. Commercially available anhydrous solvents were used for reactions conducted under inert atmosphere. Reagent grade solvents were used in all other cases, unless otherwise specified. The methyl isocyanate resin was supplied by Nova-Biochem (Cat. No. 01-64-0169). Analytical LCMS was performed on a Waters ZQ mass spectrometer connected to an Agilent 1100 HPLC system. Analytical HPLC was performed on an Agilent 1100 system. High-resolution mass spectra (HRMS) were obtained on an Agilent MSD-TOF connected to an Agilent 1100 HPLC system. During the analyses the calibration was checked by two masses and automatically corrected when needed. Spectra are acquired in positive electrospray mode. The acquired mass range was m/z 100-1100. Profile detection of the mass peaks was used. Flash chromatography was performed on a Flash Master Personal system equipped with Strata SI-1 silica gigatubes. Reverse phase chromatography was performed on a Gilson system equipped with Merck LiChoprep® RP-18 (40-63 µm) 460× 26 mm column, 30 mL/min, gradient of methanol in water. Preparative HPLC was performed on a Gilson system equipped with Phenomenex Hydro RP 15 0×20 mm, 20 mL/min, gradient of acetonitrile in water. The compounds were automatically named using ACD 6.0 or 8.0.

Analytical HPLC and LCMS data were obtained with:
System A: Phenomenex Synergi Hydro RP, (150×4.6 mm, 4 µm), gradient 5-100% CH$_3$CN (+0.085% TFA) in H$_2$O (+0.1% TFA), 1.5 mL/min, with a gradient time of 7 min, 200-300 nm, 30° C.; or
System B: Phenomenex Synergi Hydro RP, (150×4.6 mm, 4 µm), gradient 5-95% CH$_3$CN (+0.085% TFA) in H$_2$O (+0.1% TFA), 1 mL/min, with a gradient time of 15.5 min, 200-300 nm, 40° C.

Analytical LCMS data were also obtained with:
System C: Phenomenex Synergi Hydro RP(30×4.6 mm, 4 µm), gradient 5-100% CH$_3$CN (+0.085% TFA) in H$_2$O (+0.1% TFA), 1.5 mL/min, with a gradient time of 1.75 min, 30° C.

Intermediate 1

4-Nitrophenyl 4-(4-methyl)phenylpiperazine-1-carboxylate

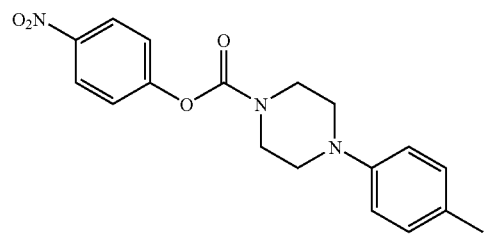

To a solution of 1-(4-methylphenyl)piperazine dihydrochloride (10.65 g, 42.7 mmol) and DIPEA (22 mL, 133 mmol) in DCM (100 mL) at 0° C. was added 4-nitrophenyl chloroformate (9.5 g, 47.1 mmol). The reaction mixture was stirred for 30 minutes at 0° C. and then washed with saturated sodium hydrogen carbonate solution (3×200 mL), dried (MgSO$_4$) and concentrated in vacuo to give 4-nitrophenyl 4-(4-methyl)phenylpiperazine-1-carboxylate (17.84 g, quantitative) as a yellow solid which was used without further purification.

Analytical LCMS: purity ~90% (System C, R$_T$=2.20 min), ES$^+$: 342.1 [MH]$^+$.

Intermediate 2

4-Nitrophenyl 4-phenylpiperazine-1-carboxylate

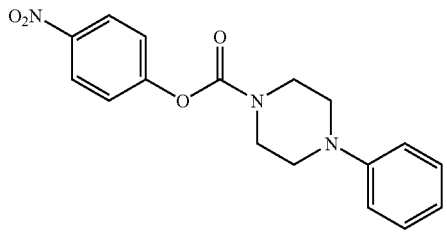

To a solution of phenylpiperazine (12.0 g, 74.0 mmol) and DIPEA (13.5 mL, 81.6 mmol) in DCM (70 mL) at 0° C. add 4-nitrophenyl chloroformate (16.5 g, 81.71 mmol). The reaction mixture was stirred for 30 minutes at 0° C. and then washed with saturated sodium hydrogen carbonate solution (3×200 mL), dried (MgSO$_4$) and concentrated in vacuo to give a 4-nitrophenyl 4-phenylpiperazine-1-carboxylate (24.8 g, 102%) as a yellow solid which was used without further purification.

Analytical LCMS: purity ~90% (System C, R$_T$=2.40 min), ES$^+$: 328.1 [MH]$^+$.

Intermediate 3

1,4-Dimethyl-(S)-2-hydroxymethyl Piperazine

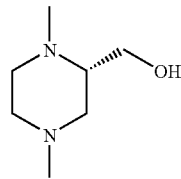

(S)-2-piperazine carboxylic acid dihydrochloride (5.10 g, 25.1 mmol) was dissolved in water (10 mL) and dioxane (40 mL) and cooled to 0° C. Sodium hydroxide (3.10 g, 77.5 mmol) in water (6 mL) and di-tert-butyl dicarbonate (11.5 g, 52.7 mmol) were added. The reaction mixture was stirred at room temperature for 16 hours and then concentrated in vacuo. The residue was suspended in DCM (400 mL), stirred for 30 minutes at room temperature and then filtered. The filtrate was concentrated in vacuo to give (S)-2-piperazine-1,2,4-tricarboxylic acid 1,4-di-tert-butyl ester (9.90 g, 119%) as a white solid which was used without further purification.

Analytical LCMS: purity 100% (System C, R$_T$=2.28 min), ES$^+$: 331.1 [MH]$^+$.

(S)-2-piperazine-1,2,4-tricarboxylic acid 1,4-di-tert-butyl ester (9.90 g, 30.0 mmol) was dissolved in THF (14 mL). 1M borane in THF (90 mL, 90.0 mmol) was added at room temperature. The reaction mixture was stirred at reflux for 4 hours and then cooled to 0° C. and quenched with the drop-wise addition of methanol (100 mL) and then concentrated in vacuo to give (S)-2-hydroxymethyl-piperazine-1,4-dicarboxylic acid di-tert-butyl ester (12.07 g, 127%) as a white solid which was used without further purification.

Analytical LCMS: purity 100% (System C, R$_T$=2.08 min), ES$^+$: 339.4 [MH]$^+$.

(S)-2-hydroxymethyl-piperazine-1,4-dicarboxylic acid di-tert-butyl ester (5.66 g, 17.9 mmol) was dissolved in THF (10 mL) and cooled to 0° C. 2M LiAlH$_4$ in THF (28.5 mL, 57.0 mmol) was added. The reaction mixture was stirred at reflux for 4 hours and then cooled to 0° C. and quenched with the drop-wise addition of 1M sodium hydroxide solution (20 mL). The reaction mixture was diluted with THF (50 mL), filtered and the filtrate was concentrated in vacuo to give 1,4-dimethyl-(S)-2-hydroxymethyl piperazine (1.44 g, 56%) as a colourless oil which was used without further purification.

Analytical LCMS: purity ~90% (System C, R$_T$=0.38 min), ES$^+$: 145.2 [MH]$^+$.

Intermediate 4

1,4-Dimethyl-(R)-2-hydroxymethyl Piperazine

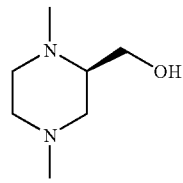

(R)-piperazine-1,3-dicarboxylic acid 1-tert-butyl ester (4.94 g, 21.5 mmol) was dissolved in water (10 mL) and dioxane (20 mL) and cooled to 0° C. Sodium hydroxide (1.72 g, 43.0 mmol) in water (4 mL) and di-tert-butyl dicarbonate (5.20 g, 23.8 mmol) were added. The reaction mixture was stirred at room temperature for 16 hours and then concentrated in vacuo. The residue was suspended in DCM (400 mL) and stirred for 30 minutes at room temperature, filtered and the filtrate was concentrated in vacuo to give (R)-2-piperazine-1,2,4-tricarboxylic acid 1,4-di-tert-butyl ester (9.78 g, 138%) as a pale yellow oil which was used without further purification.

Analytical LCMS: purity ~90% (System C, R$_T$=1.56 min), ES$^+$: 131.7 [M+H−2Boc]$^+$.

(R)-2-piperazine-1,2,4-tricarboxylic acid 1,4-di-tert-butyl ester (2.16 g, 6.55 mmol) was dissolved in THF (10 mL). 1M borane in THF (20 mL, 20.0 mmol) was added at room temperature. The reaction mixture was stirred at reflux for 4 hours and then cooled to 0° C. and quenched with the drop-wise addition of methanol (60 mL) and then concentrated in vacuo to give (R)-2-hydroxymethyl-piperazine-1,4-dicarboxylic acid di-tert-butyl ester (2.60 g, 125%) as an off white solid which was used without further purification.

Analytical LCMS: purity ~90% (System C, R$_T$=2.06 min), ES$^+$: 116.9 [M+H−2Boc]$^+$.

(R)-2-hydroxymethyl-piperazine-1,4-dicarboxylic acid di-tert-butyl ester (6.24 g, 19.7 mmol) was dissolved in THF (10 mL) and cooled to 0° C. 2M LiAlH$_4$ in THF (30.0 mL, 60.0 mmol) was added. The reaction mixture was stirred at reflux for 4 hours and then cooled to 0° C. and quenched with the drop-wise addition of 1M sodium hydroxide solution (20 mL). The reaction mixture was diluted with THF (50 mL), filtered and the filtrate was concentrated in vacuo to give 1,4-dimethyl-(R)-2-hydroxymethyl piperazine (1.77 g, 62%) as a colourless oil which was used without further purification.

Analytical LCMS: purity 100% (System C, R$_T$=0.44 min), ES$^+$: 145.2 [MH]$^+$.

Intermediate 5

(S)-(4-Methyl-piperazin-2-yl)-methanol

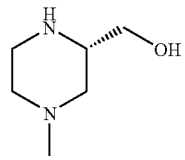

To a stirred suspension of (S)-piperazine-1,3-dicarboxylic acid 1-tert-butyl ester (5.00 g, 21.7 mmol) in THF (40 mL) was slowly added 1.0 M borane-THF complex solution (32.6 mL, 32.6 mmol). The reaction was heated to 90° C. and stirred under reflux for 2 hours. The reaction mixture was removed from the heat before a further 1.5 equivalents of 1.0 M borane·THF complex solution (32.6 mL, 32.6 mmol) was added. The reaction was re-heated to 90° C. and stirred under reflux for a further 2 hours. The reaction was cooled to 0° C. and quenched by the slow addition of MeOH. The reaction mixture was then concentrated in vacuo. The white solid obtained was dissolved in THF (30 mL), cooled to 0° C. and slowly added a 2.0M solution of LiAlH$_4$ in THF (27 mL, 54.0 mmol). The reaction was heated to 90° C. and stirred under reflux for 2 h. A further portion of 2.0M solution of LiAlH$_4$ in THF (27 mL, 54.0 mmol) was added and the reaction stirred under reflux for 4 h and then at room temperature overnight. The reaction mixture was cooled to 0° C. and quenched by the slow addition of 1.0M aq NaOH solution until the exothermic reaction subsided. The resulting gel was diluted with THF and the solids filtered off. The filtrate was then concentrated in vacuo to afford (S)-(4-methyl-piperazin-2-yl)-methanol (2.84 g, 101% crude yield) as a colourless oil.

Intermediate 6

4-(4-Fluorophenyl)-piperazine-1-carboxylic Acid 4-nitrophenyl Ester

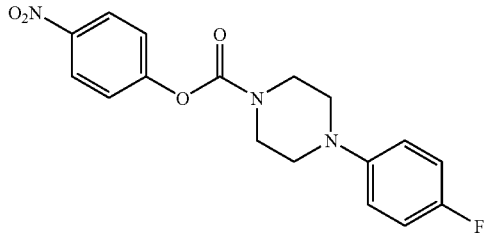

1-(4-Fluoro-phenyl)-piperazine (12.2 g, 67.7 mmol) and triethylamine (4.63 mL, 67.7 mmol) were dissolved in anhydrous THF (150 mL) under nitrogen and the reaction mixture was cooled to 0° C. 4-Nitrophenyl chloroformate (13.4 g, 67.7 mmol) dissolved in anhydrous THF (150 mL) at 0° C. was added and the reaction mixture was stirred at room temperature overnight. The solvent was removed in vacuo and the residue suspended between water and EtOAc. The aqueous layer was extracted with two further portions of EtOAc, the organic layers were combined, dried (MgSO$_4$), dried in vacuo and then recrystallised from toluene (50 mL)/hexane (60 mL) to give 4-(4-fluorophenyl)-piperazine-1-carboxylic acid 4-nitrophenyl ester (15.8 g, 67%) as fine yellow needles.

Intermediate 7

3-Hydroxymethyl-morpholine-4-carboxylic Acid tert-butyl Ester

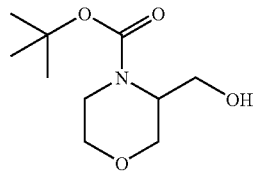

Morpholine-3,4-dicarboxylic acid 4-tert-butyl ester (9.50 g, 41 mmol) was dissolved in anhydrous THF (50 mL) under nitrogen and cooled to −10° C. A 1M solution of borane (82 mL, 82 mmol) was added dropwise whilst maintaining the temperature below 0° C. The reaction mixture was allowed to warm to room temperature and stirred overnight. The reaction mixture was cooled to −5° C. and water (10 mL) was added cautiously followed by Na$_2$CO$_3$ (9.5 g) in water (20 mL). After stirring for 30 min at room temperature the THF was removed in vacuo, water was added and the reaction mixture was extracted with diethylether (×3). The combined organic extracts were dried (MgSO$_4$) and the solvent was evaporated in vacuo to give 3-hydroxymethyl-morpholine-4-carboxylic acid tert-butyl ester (8.9 g, 100%) as a colourless oil.

Intermediate 8

(S)-2-Hydroxymethyl-morpholine-4-carboxylic Acid tert-butyl ester

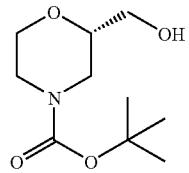

(S)-3-Amino-1,2-propanediol (16.8 g, 184 mmol) was dissolved in MeOH (90 mL) at room temperature and the solution was diluted with MeCN (550 mL). NEt$_3$ (30.5 mL, 219 mmol) was added and the reaction mixture was cooled to −10° C. Chloroacetyl chloride (22.2 g, 15.6 mL, 197 mmol) was added dropwise at −10° C. during 1.5 h under nitrogen. The temperature was maintained at −10° C. for an additional hour and then the reaction mixture was allowed to reach room temperature and stirred overnight (16 h). The solvents were removed in vacuo. The residue was purified by column chromatography (normal phase, Apollo Scientific silica, 40-60µ, 60 Å, gradient 1% to 10% MeOH in EtOAc). The combined fractions were evaporated to afford 2-chloro-N—[(S)-2,3-dihydroxypropyl]-acetamide (28.5 g, 92%) as a colourless oil which gave a white solid on standing.

To a solution of t-BuOK (13.7 g, 122 mmol) in t-AmOH (175 mL) was added a solution of 2-chloro-N—[(S)-2,3-dihydroxypropyl]acetamide (8.1 g, 48.3 mmol) in t-AmOH (325 mL) at room temperature over 2 h. The resulting suspension was stirred for 1 h at room temperature. Methanol (50 mL) and water (5 mL) were added and the resulting solution was stirred for 0.5 h at room temperature before adjusting the pH to 5 by the addition of conc. HCl. The suspension was filtered and the solid washed with methanol. The filtrate was evaporated in vacuo, the resulting solid was slurried in methanol (50 mL) and filtered off to afford (S)-6-(hydroxymethyl)

morpholin-3-one (1.3 g) as a white solid. A second crop was obtained by adding EtOAc (200 mL) to the filtrate and filtering the resulting solution through a silica plug (1×10 cm). The solvent was evaporated in vacuo to afford (S)-6-(hydroxymethyl)morpholin-3-one (3.9 g, overall yield 5.2 g, 82%) as a white solid.

To a solution of (S)-6-(hydroxymethyl)morpholin-3-one (7.50 g, 57.2 mmol) in anhydrous THF (100 mL) at 0° C. was added $BH_3$ in THF (110 mL, 85.8 mmol). The reaction mixture was allowed to reach room temperature and then heated at reflux overnight. The reaction was cooled to room temperature and then quenched with a mixture of water (5 mL) in THF (16 mL) followed by 7M methanolic ammonia (30 mL). The reaction mixture was heated to reflux for 30 min, cooled and the solvents removed in vacuo. The residue was dissolved in methanol (15 mL), loaded onto an Isolute SCX-2 20 g column, washed with MeOH (100 mL) and eluted with methanolic ammonia. The solvent was removed in vacuo to give (S)-morpholin-2-yl-methanol (1.67 g, 24%) as a brown liquid.

To a solution of (S)-morpholin-2-yl-methanol (1.63 g, 13.9 mmol) in DCM (75 mL) was added a solution of NaOH (0.61 g, 15.3 mmol) in water (2 mL). Di-tert-butyldicarbonate (3.04 g, 13.9 mmol) was added and the reaction mixture stirred overnight at room temperature. The aqueous phase was separated and further extracted with DCM (2×15 mL). The combined organic phases were dried ($Na_2SO_4$) and the solvent removed in vacuo. The residue was purified by column chromatography (normal phase silica, 20 g Isolute-Si column, gradient 1% to 10% MeOH in DCM) and dried in vacuo to give (S)-2-hydroxymethyl-morpholine-4-carboxylic acid tert-butyl ester (2.3 g, 71%) as a white solid.

Intermediate 9

(R)-2-Hydroxymethyl-morpholine-4-carboxylic Acid tert-butyl Ester

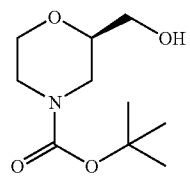

(R)-2-hydroxymethyl-morpholine-4-carboxylic acid tert-butyl ester was prepared similar to the procedure described for Intermediate 8, but using (R)-3-amino-1,2-propanediol instead of (S)-3-amino-1,2-propanediol. The title compound was obtained as a white solid (10% overall yield, 4 steps).

Intermediate 10

(S)-(4-Methylmorpholin-2-yl)-methanol

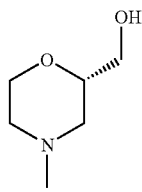

(S)-2-Hydroxymethyl-morpholine-4-carboxylic acid tert-butyl ester (Intermediate 8; 1.20 g, 5.52 mmol) in THF (5 mL) was added to a suspension of $LiAlH_4$ (1.30 g, 34.3 mmol) in anhydrous THF (15 mL) at −10° C. and stirred under nitrogen for 15 min. The cooling bath was removed and the reaction mixture was gently heated to reflux for 4 h. The reaction mixture was quenched by careful addition of a mixture of water (4 mL) in THF (25 mL) with ice bath cooling. THF (50 mL) was added to the reaction mixture, stirred for 15 min, filtered and the solid washed with THF (50 mL). The combined filtrates were evaporated in vacuo. The residue was dissolved in DCM (50 mL), dried ($MgSO_4$) and the solvent removed in vacuo to give (S)-(4-methylmorpholin-2-yl)-methanol (490 mg, 67%) as a colourless oil.

Intermediate 11

(R)-(4-Methylmorpholin-2-yl)-methanol

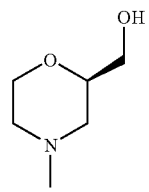

(R)-(4-Methylmorpholin-2-yl)-methanol was prepared similar to the procedure described for Intermediate 10, but using (R)-2-hydroxymethyl-morpholine-4-carboxylic acid tert-butyl ester (Intermediate 9) instead of (S)-2-hydroxymethyl-morpholine-4-carboxylic acid tert-butyl ester (Intermediate 8). The title compound was obtained as a colourless oil (560 mg, 77%).

Intermediate 12

4-(2,4-Difluorophenyl)-piperazine-1-carboxylic Acid 4-nitrophenyl Ester

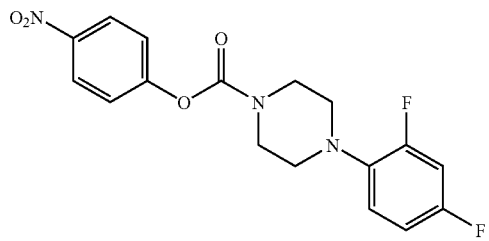

1-(2,4-Difluoro-phenyl)-piperazine (3.70 g, 18.9 mmol) and triethylamine (2.8 mL, 19.8 mmol) were dissolved in anhydrous THF (30 mL) under nitrogen and the reaction mixture was cooled to 0° C. 4-Nitrophenyl chloroformate (3.8 g, 18.9 mmol), dissolved in anhydrous THF (25 mL), was added dropwise and the reaction mixture was stirred at room temperature overnight. The solvent was removed in vacuo and the residue triturated with water, and then filtered. The yellow solid was recrystallised from a mixture of hexane and toluene(3:7) using charcoal to give 4-(2,4-difluorophenyl)-piperazine-1-carboxylic acid 4-nitrophenyl ester (4.3 g, 63%) as a yellow crystalline solid.

Intermediate 13

2-(1,4-Dimethylpiperazin-2-yl)ethanol

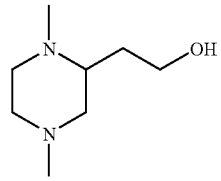

To a solution of methyl-2-piperazineacetate dihydrochloride (500 mg, 2.16 mmol) in dioxane (12 mL) and water (6.0 mL) at 0° C. was slowly added a solution of NaOH (182 g, 4.55 mmol) in water (0.4 mL) followed by di-tert-butyl dicarbonate (992 mg, 4.55 mmol). The reaction mixture was stirred at room temperature for 4 hours, and then concentrated in vacuo. To the resulting salts was added DCM (75 mL) and the suspension stirred vigorously for 30 minutes. The salts were filtered off and washed with DCM (50 mL). The filtrate was concentrated in vacuo to afford 2-methoxycarbonylmethylpiperazine-1,4-dicarboxylic acid di-tert-butyl ester (662 mg, 85%) as a pale yellow oil.

To a stirred solution of 2-methoxycarbonylmethylpiperazine-1,4-dicarboxylic acid di-tert-butyl ester (662 mg, 1.85 mmol) in anhydrous THF (10 mL) at 0° C. was slowly added a 1M solution of LiAlH$_4$ in THF (5.7 mL, 5.70 mmol). The stirred reaction mixture was allowed to warm to room temperature over a period of 15 minutes before being refluxed for 2 hours. After this time the reaction mixture was cooled to 0° C. and cautiously quenched by the dropwise addition of 1.0M aqueous NaOH solution until the effervescing ceased. The resulting gel was diluted with THF (50 mL) and the solids filtered off. The filtrate was concentrated in vacuo to afford 2-(1,4-dimethylpiperazin-2-yl)ethanol (191 mg, 65%) as a colourless oil.

Example 1

[(3R)-1-Methylpiperidin-3-yl]methyl 4-(4-methylphenyl)piperazine-1-carboxylate

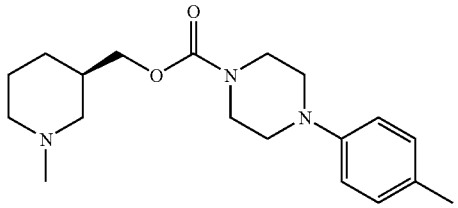

A 2M solution of LiAlH$_4$ in THF (14.0 mL, 28.0 mmol) was added drop-wise to a solution of (R)-tert-butyl 3-(hydroxymethyl)piperidine-1-carboxylate (5.00 g, 23.2 mmol) in THF (30 mL) under argon at 0° C. The reaction mixture was allowed to warm to room temperature over 2 hours and stirred at room temperature for 17 hours. The reaction mixture was cooled to 0° C. and a 1M aq NaOH solution (4.0 mL) was added drop-wise. Water (2 mL) was added and the resulting mixture stirred at room temperature for 2 hours. The white solid was removed by filtration. The filtrate was concentrated in vacuo to give (R)-(1-methylpiperidin-3-yl)methanol (3.19 g, 106%) as a colourless oil which was used without further purification.

Analytical LCMS: purity ~90% (System C, R$_T$=0.46 min), ES$^+$: 130.1 [MH]$^+$.

Sodium hydride (0.70 g, 60% dispersion in mineral oil, 17.5 mmol) was suspended in heptane (10 mL) under an argon atmosphere. The heptane was decanted off, and the flask was charged with THF (20 mL) and cooled to 0° C. A solution of (R)-(1-methylpiperidin-3-yl)methanol (0.75 g, 5.83 mmol) in THF (20 mL) was added drop-wise, followed by a solution of 4-nitrophenyl 4-(4-methylphenyl)piperazine-1-carboxylate (Intermediate 1; 2.19 g, 6.42 mmol) in THF (20 mL). The reaction mixture was allowed to warm to room temperature and stirred for 18 hours. The reaction mixture was then cooled to 0° C. and quenched with the drop-wise addition of sat aq NaHCO$_3$ solution and concentrated in vacuo. The residue was dissolved in ethyl acetate (200 mL), washed with sat aq NaHCO$_3$ solution (4×50 mL), dried (MgSO$_4$) and concentrated in vacuo. The residue was purified by reverse phase chromatography (gradient eluting with methanol in water, with 1% formic acid in each solvent, 0-25%). The resulting residue was dissolved in DCM (50 mL) and stirred with solid K$_2$CO$_3$ for 20 min, filtered and concentrated in vacuo. The residue was further purified by normal phase column chromatography (eluting with DCM, followed by a 90:10 mixture of DCM:MeOH) to give [(3R)-1-methylpiperidin-3-yl]methyl 4-(4-methylphenyl)piperazine-1-carboxylate (619 mg, 32%) as a pale brown solid.

Analytical HPLC: purity 99.9% (System A, R$_T$=4.07 min); Analytical LCMS: purity 100% (System A, R$_T$=4.46 min), ES$^+$: 332.5 [MH]$^+$; HRMS calcd for C$_{19}$H$_{29}$N$_3$O$_2$:331.2260, found 331.2275.

Example 2

[(3S)-1-Methylpiperidin-3-yl]methyl 4-(4-methylphenyl)piperazine-1-carboxylate

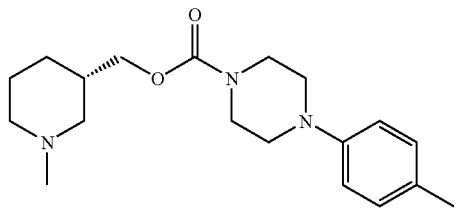

(S)-(1-Methylpiperidin-3-yl)methanol (1.50 g, 11.6 mmol; prepared according to Example 1 but starting from (S)-tert-butyl 3-(hydroxymethyl)piperidine-1-carboxylate) was dissolved in DCM (20 mL) and cooled to 0° C. NMM (1.30 mL, 12.2 mmol) and nitrophenyl chloroformate (2.46 g, 12.2 mmol) were added. The reaction mixture was stirred at 0° C. for 2 hours and then a solution of 4-(4-methylphenyl)piperazine dihydrochloride (1.88 g, 7.5 mmol) and DIPEA (3.70 mL, 22.1 mmol) in DMF (40 mL) was added. The reaction mixture was stirred at room temperature for 2 hours and then concentrated in vacuo. The residue was dissolved in EtOAc (300 mL) and then washed sequentially with 1M aq Na$_2$CO$_3$ solution (5×200 mL), dried (MgSO$_4$) and concentrated in vacuo. The residue was purified by normal phase column chromatography (eluting with DCM, followed by a 85:15 mixture of DCM:MeOH) followed by reverse phase HPLC (Advanced Chromatography Technologies ACE-122-1030 RP silica 100×30 mm column, packed with Ace 5 C8 (5 µm), Pore Size 100 Å, 30 mL/min, gradient of CH$_3$CN in water, with 0.1% TFA in each solvent, 8-38%). The residue was dissolved in DCM (70 mL) and stirred with solid K$_2$CO$_3$ for 20 min, filtered and concentrated in vacuo to give a yellow oil which was recrystallised from heptane/EtOAc to give [(3S)-1-methylpiperidin-3-yl]methyl 4-(4-methylphenyl)piperazine-1-carboxylate (521 mg, 13.5%) as a white solid.

Analytical HPLC: purity 100% (System A, $R_T$=3.88 min); Analytical LCMS: purity 100% (System A, $R_T$=4.39 min), ES$^+$: 332.2 [MH]$^+$; HRMS calcd for $C_{19}H_{29}N_3O_2$:331.2260, found 331.2270.

Example 3

[(2S)-1,4-Dimethylpiperazin-2-yl]methyl 4-phenylpiperazine-1-carboxylate

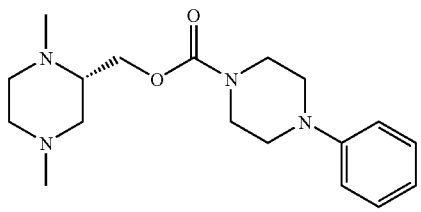

To a solution of 1,4-dimethyl-(S)-2-hydroxymethyl piperazine (Intermediate 3; 1.49 g, 10.3 mmol) in THF (20 mL) at 0° C. was added sodium hydride (1.24 g, 60% dispersion in mineral oil, 31.0 mmol). The reaction mixture was stirred for several minutes at 0° C. and then 4-nitrophenyl 4-phenylpiperazine-1-carboxylate (Intermediate 2; 3.72 g, 11.4 mmol) in THF (20 mL). The reaction mixture was allowed to warm to room temperature and stirred for 7 hours. The reaction mixture was then cooled to 0° C. and quenched with the drop-wise addition of sat aq NaHCO$_3$ solution. The THF was removed in vacuo, the aqueous phase extracted with EtOAc (×3), combined organic phases washed with sat aq NaHCO$_3$ solution (×6), dried (MgSO$_4$) and concentrated in vacuo. The residue was suspended in water: formic acid solution [1:1] (20 mL), filtered and the filtrate was purified by reverse phase column chromatography (gradient eluting with methanol in water, with 1% formic acid in each solvent, 0-15%). The resulting residue was dissolved in DCM (50 mL) and stirred with solid K$_2$CO$_3$ for 20 minutes, filtered and concentrated in vacuo to give [(2S)-1,4-dimethylpiperazin-2-yl]methyl 4-phenylpiperazine-1-carboxylate (1.25 g, 36%) as a pale yellow solid.

Analytical HPLC: purity 99.8% (System A, $R_T$=3.50 min); Analytical LCMS: purity 100% (System A, $R_T$=3.86 min), ES$^+$: 333.6 [MH]$^+$; HRMS calcd for $C_{18}H_{28}N_4O_2$:332.2212, found 332.2227.

Example 4

[(2R)-1,4-Dimethylpiperazin-2-yl]methyl 4-phenylpiperazine-1-carboxylate

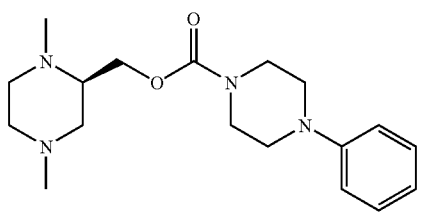

Sodium hydride (1.14 g, 60% dispersion in mineral oil, 28.6 mmol) was suspended in heptane (10 mL) under an argon atmosphere. The heptane was decanted off, and the flask was charged with THF (20 mL) and cooled to 0° C. A solution of 1,4-dimethyl-(R)-2-hydroxymethyl piperazine (Intermediate 4; 1.38 g, 9.5 mmol) in THF (20 mL) was added drop-wise, followed by a solution of the 4-nitrophenyl 4-phenylpiperazine-1-carboxylate (Intermediate 2; 4.06 g, 12.4 mmol) in THF (20 mL). The reaction mixture was allowed to warm to room temperature, stirred for 16 hours, the reaction mixture was cooled to 0° C. then quenched with the drop-wise addition of sat aq NaHCO$_3$ solution and concentrated in vacuo. The residue was dissolved in EtOAc (200 mL), washed with sat aq NaHCO$_3$ solution (4×50 mL), dried (MgSO$_4$) and concentrated in vacuo. The residue was suspended in water:formic acid solution [1:1] (20 mL), filtered and the filtrate was purified by reverse phase column chromatography (gradient eluting with methanol in water, with 1% formic acid in each solvent, 0-15%). The resulting residue was dissolved in DCM (50 mL) and stirred with solid K$_2$CO$_3$ for 20 minutes, filtered and concentrated in vacuo to give [(2R)-1,4-dimethylpiperazin-2-yl]methyl 4-phenylpiperazine-1-carboxylate (1.93 g, 61%) as a pale yellow solid.

Analytical HPLC: purity 100% (System A, $R_T$=3.55 min); Analytical LCMS: purity 100% (System A, $R_T$=3.90 min), ES$^+$: 333.5 [MH]$^+$; HRMS calcd for $C_{18}H_{28}N_4O_2$:332.2212, found 332.2225.

Example 5

[(2S)-1,4-Dimethylpiperazin-2-yl]methyl 4-(4-fluorophenyl)piperazine-1-carboxylate

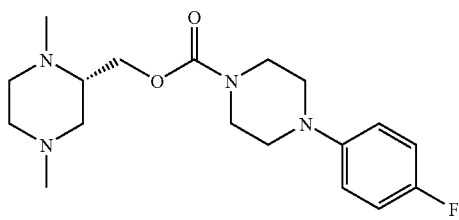

4-Nitrophenyl chloroformate (5.17 g, 25.7 mmol) was dissolved in DCM (200 mL) at room temperature and the reaction mixture was cooled to 0° C. and DIPEA (6.94 g, 9.38 mL, 53.9 mmol) and 1,4-dimethyl-(S)-2-hydroxymethyl piperazine (Intermediate 3; 3.70 g, 25.7 mmol) were added. The reaction mixture was stirred at room temperature for 2 h, and then split into three equal volumes. To one portion was added 1-(4-fluoro-phenyl)-piperazine (1.53 g, 8.5 mmol) and the mixture was stirred for 48 h. The solvent was removed in vacuo and the residue partitioned between EtOAc (500 mL) and 1.0M NaOH solution (200 mL). The organic layer was washed with 10M aq NaOH solution (5×125 mL), brine (100 mL), dried (MgSO$_4$) and the solvent removed in vacuo. The residue was dissolved in DCM (100 mL) and isocyanate resin (3 g) was added, the reaction mixture was shaken for 14 h, filtered and the solvent was removed in vacuo. The residue was purified by reverse phase column chromatography (LiChroprep RP-18, 40-63 μm, 460×26 mm (100 g), 30 mL/min, gradient 0% to 30% (over 75 min) to 100% (over 13 min) MeOH in water with 1% formic acid). The residue was desalted using K$_2$CO$_3$ in DCM to give [(2S)-1,4-dimethylpiperazin-2-yl]methyl 4-(4-fluorophenyl)piperazine-1-carboxylate (1.78 g, 60.0%) as a light yellow gum.

Analytical HPLC: purity 99.1% (System A, $R_T$=3.69 min); Analytical LCMS: purity 100% (System A, $R_T$=4.10 min), ES$^+$: 351.1 [MH]$^+$.

Example 6

4-Phenylpiperazine-1-carboxylic acid 2-(1,4-dimethylpiperazin-2-yl)ethyl Ester

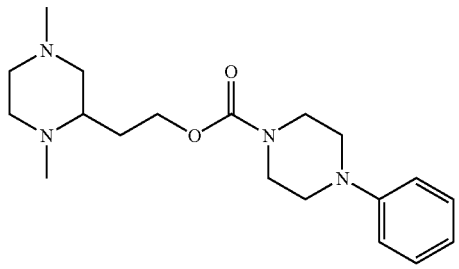

2-(1,4-Dimethylpiperazin-2-yl)ethanol (703 mg, 4.44 mmol) was dissolved in anhydrous THF (20 mL) and the stirred solution cooled to 0° C. before NaH (60% dispersion in mineral oil; 550 mg, 13.8 mmol) was added. The suspension was left to stir for 10 minutes. 4-Nitrophenyl 4-phenylpiperazine-1-carboxylate (Intermediate 2; 1.89 g, 5.77 mmol) was added to the reaction mixture, which was left to stir at room temperature for 3 hours. After this time the reaction was terminated by cooling the mixture to 0° C. and cautiously quenching with saturated aqueous NaHCO$_3$ solution (50 mL). The THF was removed in vacuo and transferred to a separating funnel where the organic product was extracted with EtOAc (3×75 mL). The combined organic extracts were collected together and washed with saturated aqueous NaHCO$_3$ solution (3×75 mL). The organic layer was dried (MgSO$_4$), filtered and concentrated in vacuo to give a crude yellow slurry. The crude residue was purified by reverse phase column chromatography (LiChroprep RP-18, 40-63 μm, 460×26 mm (100 g), 30 mL/min, gradient 0% to 15% (over 70 min) to 100% (over 5 min) MeOH in water with 1% formic acid). De-salting (using K$_2$CO$_3$ in DCM), filtration and concentration in vacuo afforded 4-phenylpiperazine-1-carboxylic acid 2-(1,4-dimethylpiperazin-2-yl)ethyl ester (236 mg, 13%) as a dark yellow oil.

Analytical HPLC: purity 100% (System A, $R_T$=3.50 min); Analytical LCMS: purity 100% (System A, $R_T$=3.92 min), ES$^+$: 347.6 [MH]$^+$; HRMS calcd for C$_{19}$H$_{30}$N$_4$O$_2$:346.2369, found 346.2378.

Example 7

[(2S)-1,4-Dimethylpiperazin-2-yl]methyl 4-(2,4-difluorophenyl)piperazine-1-carboxylate

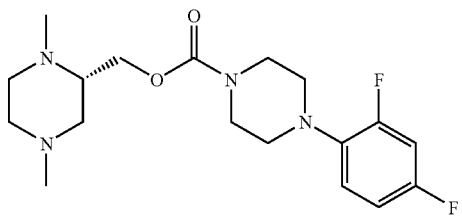

4-Nitrophenyl chloroformate (5.17 g, 25.7 mmol) was dissolved in DCM (200 mL) at room temperature and the reaction mixture was cooled to 0° C. and DIPEA (6.94 g, 9.38 mL, 53.9 mmol) and 1,4-dimethyl-(S)-2-hydroxymethyl piperazine (Intermediate 3; 3.70 g, 25.7 mmol) were added. The reaction mixture was stirred at room temperature for 2 h and then split into three equal volumes. To one portion was added 1-(2,4-difluoro-phenyl)-piperazine (1.68 g, 8.5 mmol) and stirred for 48 h. The solvent was removed in vacuo and the residue was partitioned between EtOAc (500 mL) and 1.0M aq NaOH solution (200 mL). The organic layer was washed with 1.0M aq NaOH solution (5×125 mL), brine (100 mL), dried (MgSO$_4$) and the solvent removed in vacuo. The residue was dissolved in DCM (100 mL) and isocyanate resin (3 g) was added, the reaction mixture was shaken for 14 h, filtered and the solvents were removed in vacuo. The residue was purified by reverse phase column chromatography (LiChroprep RP-18, 40-63 μm, 460×26 mm (100 g), 30 mL/min, gradient 0% to 30% (over 75 min) to 100% (over 13 min) MeOH in water with 1% formic acid). The residue was de-salted using K$_2$CO$_3$ in DCM to give [(2S)-1,4-dimethylpiperazin-2-yl]methyl 4-(2,4-difluorophenyl)piperazine-1-carboxylate (1.23 g, 39.4%) as a light yellow gum.

Analytical HPLC: purity 100% (System A, $R_T$=4.12 min); Analytical LCMS: purity 100% (System A, $R_T$=4.53 min), ES$^+$: 369.1 [MH]$^+$; HRMS calcd for C$_{18}$H$_{26}$F$_2$N$_4$O$_2$: 368.2024, found 368.2038.

Example 8

[(2S)-4-Methylpiperazin-2-yl]methyl 4-phenylpiperazine-1-carboxylate Trihydrochloride

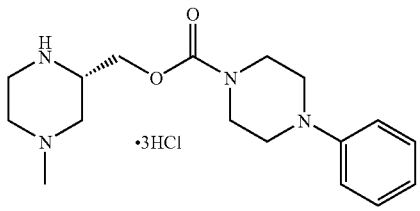

To a suspension of (S)-(4-methyl-piperazin-2-yl)-methanol (Intermediate 5; 2.84 g, 21.7 mmol) in a mixture of H$_2$O (20 mL) and dioxane (40 mL) at 0° C. was added 50% w/w aq NaOH solution (0.96 g, 24.0 mmol). Di-tert-butyl dicarbonate (5.01 g, 22.9 mmol) was added and the reaction mixture stirred at room temperature overnight. The solvents were removed in vacuo. The residue was dissolved in anhydrous THF (25 mL) and the solution cooled to 0° C. NaH (60% wt dispersion in oil; 4.05 g, 101 mmol) was added and the grey suspension stirred for 10 minutes before 4-nitro-phenyl 4-phenyl-piperazine-1-carboxylate (Intermediate 2; 11.2 g, 34.1 mmol) was added. The reaction was stirred at room temperature over the weekend. The reaction mixture was cooled to 0° C. and quenched with sat aq NaHCO$_3$ solution (20 mL) before the THF was removed in vacuo. The organic product was extracted with EtOAc (3×50 mL) and the organic layers combined and washed with sat aq NaHCO$_3$ solution (3×50 mL), dried (MgSO$_4$), and the solvent removed in vacuo. MeOH was added to the crude slurry and the solids filtered off and washed with MeOH. The filtrate was concentrated and purified in two batches by reverse phase column chromatography (LiChroprep RP-18, 40-63 μm, 460×26 mm (100 g), 30 mL/min, gradient 0% to 50% (over 75 min) MeOH in water with 1% formic acid). The product was de-salted using K$_2$CO$_3$ in DCM to give (S)-4-methyl-2-(4-phenyl-piperazine-1-carbonyloxymethyl)-piperazine-1-carboxylic acid tert-butyl ester (1.65 g, 18%) as a brown oil.

To a solution of (S)-4-methyl-2-(4-phenyl-piperazine-1-carbonyloxymethyl)-piperazine-1-carboxylic acid tert-butyl ester (1.65 g, 3.9 mmol) in MeOH (10 mL) was added 2M HCl in Et$_2$O solution (11.8 mL, 23.6 mmol). The reaction was stirred at room temperature for 3 days. The reaction mixture was concentrated in vacuo. The residue was purified by reverse phase column chromatography (LiChroprep RP-18, 40-63 μm, 460×26 mm (100 g), 30 mL/min, gradient 0% to 15% (over 75 min) MeOH in water with 0.1% TFA. The material was then purified further by reverse phase HPLC (YMC ODS-A 100×20 mm, 5 μm, 25 mL/min, gradient 50% to 100% (over 7 min) then 100% (3 min) MeOH in 10% MeOH/water). The pure product was stirred in 4M aq HCl solution (10 mL) for 4 hours before being concentrated in vacuo. The resulting oil was washed with heptane, concentrated in vacuo and then dried in a vacuum oven overnight to afford the [(2S)-4-methylpiperazin-2-yl]methyl 4-phenylpiperazine-1-carboxylate trihydrochloride salt (1.63 g, 96%) as a pale brown solid.

Analytical HPLC: purity 100% (System A, R$_T$=3.27 min); Analytical LCMS: purity 100% (System A, R$_T$=3.71 min), ES$^+$: 319.2 [MH]$^+$; HRMS calcd for C$_{17}$H$_{26}$N$_4$O$_2$:318.2056, found 318.2071.

Example 9

(1,4-Dimethylpiperazin-2-yl)methyl 4-benzylpiperazine-1-carboxylate

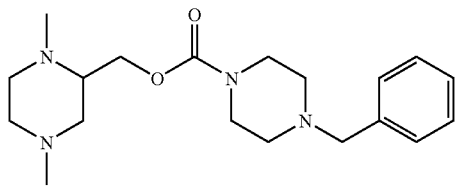

1,4-dimethyl-2-hydroxymethyl piperazine (1.00 g, 6.94 mmol) was dissolved in DCM (50 mL) at room temperature and NMM (0.74 g, 7.29 mmol) was added. The reaction mixture was cooled to 0° C. and 4-nitrophenylchloroformate (1.4 g, 6.94 mmol) was added. The reaction mixture was stirred at room temperature for 4 h and then divided into two equal volumes. To one portion was added DIPEA (1.35 g, 10.4 mmol), 1-benzyl piperazine (0.61 g, 3.47 mmol) and the reaction mixture was stirred for 4 h. The solvents were removed in vacuo and the residue was partitioned between EtOAc (300 mL) and 1.0M aq NaOH solution (100 mL). The organic layer was washed with 1.0M aq NaOH solution (5×100 mL), brine (100 mL), dried (MgSO$_4$) and the solvents were removed in vacuo. The residue was dissolved in DCM (100 mL) and isocyanate resin was added, the reaction mixture was shaken for 16 h, filtered and the solvents were removed in vacuo. The residue was purified by reverse phase column chromatography (LiChroprep RP-18, 40-63 μm, 460×26 mm (100 g), 30 mL/min, gradient 0% to 30% (over 88 min) MeOH in water with 1% formic acid). The residue was de-salted using K$_2$CO$_3$ in DCM to give (1,4-dimethylpiperazin-2-yl)methyl 4-benzylpiperazine-1-carboxylate (0.32 g, 26.3%) as a light yellow oil.

Analytical HPLC: purity 100% (System A, R$_T$=2.94 min); Analytical LCMS: purity 100% (System A, R$_T$=3.40 min), ES$^+$: 347.2 [MH]$^+$; HRMS calcd for C$_{19}$H$_{30}$N$_4$O$_2$:346.2369, found 346.2382.

Example 10

Morpholin-2-ylmethyl 4-phenylpiperazine-1-carboxylate Dihydrochloride

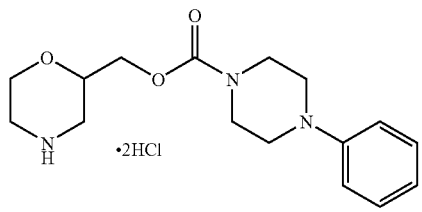

2-Hydroxymethyl-morpholine-4-carboxylic acid tert-butyl ester (4.13 g, 19.0 mmol) was dissolved in anhydrous THF (20 mL) and the solution cooled to 0° C. NaH (60% wt dispersion in oil; 2.28 g, 57.0 mmol) was added and the grey suspension stirred for 10 minutes before 4-nitrophenyl 4-phenylpiperazine-1-carboxylate (Intermediate 2; 7.46 g, 22.8 mmol) was added. The reaction was stirred at room temperature over the weekend. A further 1.5 equivalents of NaH (60% wt dispersion in oil) (1.14 g, 28.5 mmol) was added and the reaction stirred at room temperature overnight. The reaction mixture was cooled to 0° C. and quenched with sat aq NaHCO$_3$ solution (50 mL) before the THF was removed in vacuo. The organic product was extracted with EtOAc (3×50 mL) and the organic layers combined, washed with sat aq NaHCO$_3$ solution (3×50 mL), dried (MgSO$_4$) and the solvent removed in vacuo. The residue was purified by reverse phase column chromatography (LiChroprep RP-18, 40-63 μm, 460×36 mm (200 g), 30 mL/min, gradient 0% to 80% (over 120 mins) MeOH in water with 1% formic acid) to afford 2-(4-phenylpiperazine-1-carbonyloxymethyl)-morpholine-4-carboxylic acid tert-butyl ester (6.67 g, 87% yield) as a dark brown oil.

To a solution of 2-(4-phenylpiperazine-1-carbonyloxymethyl)-morpholine-4-carboxylic acid tert-butyl ester (6.67 g, 16.5 mmol) in MeOH (10 mL) was added 2M HCl in Et$_2$O solution (16.5 mL, 32.9 mmol). The brown solution was stirred at room temperature overnight. The reaction mixture was concentrated in vacuo. The residue purified by reverse phase column chromatography (LiChroprep RP-18, 40-63 μm, 460×26 mm (100 g), 30 mL/min, gradient 0% to 15% (over 75 min) MeOH in water with 0.1% TFA). The pure sample was stirred in a 4M aq HCl solution (20 mL) overnight before being concentrated in vacuo. The resulting yellow oil was washed with heptane, concentrated in vacuo and dried in a vacuum oven overnight to give the morpholin-2-ylmethyl 4-phenylpiperazine-1-carboxylate dihydrochloride salt (4.72 g, 76%) as a pale yellow solid.

Analytical HPLC: purity 99.6% (System A, R$_T$=3.57 min); Analytical LCMS: purity 100% (System A, R$_T$=3.90 min), ES$^+$: 306.5 [MH]$^+$; HRMS calcd for C$_{16}$H$_{23}$N$_3$O$_3$:305.1739, found 305.1749.

Example 11

(2S)-Morpholin-2-ylmethyl 4-phenylpiperazine-1-carboxylate

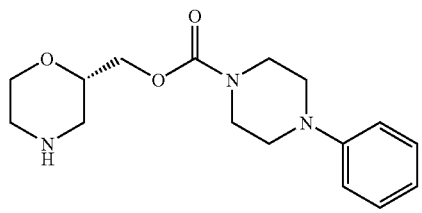

(S)-2-Hydroxymethyl-morpholine-4-carboxylic acid tert-butyl ester (Intermediate 8; 100 mg, 0.46 mmol) was added to a suspension of NaH (60% dispersion in oil; 55.0 mg, 1.38 mmol) in anhydrous THF (5 mL) and stirred under nitrogen for 30 min. 4-Nitrophenyl 4-phenylpiperazine-1-carboxylate (Intermediate 2, 180 mg, 0.55 mmol) and THF (2 mL) were added and the reaction mixture was stirred at room temperature for 48 h. The reaction mixture was filtered through celite and the solid washed with THF (10 mL). The filtrates were combined and the solvent removed in vacuo. The residue was purified by column chromatography (normal phase silica, 5 g Isolute-Si column, gradient 10% to 30% EtOAc in hexane) to give (2S)-(4-phenylpiperazine-1-carbonyloxymethyl)-morpholine-4-carboxylic acid tert-butyl ester (180 mg, 96%) as a colourless oil.

(2S)-(4-Phenylpiperazine-1-carbonyloxymethyl)-morpholine-4-carboxylic acid tert-butyl ester (180 mg, 0.44 mmol) was dissolved in DCM (2 mL) and TFA (3 mL, 10% in DCM) was added. The reaction mixture was stirred at room temperature overnight. The solvents were removed in vacuo. Heptane was added and the solvent was removed in vacuo. $K_2CO_3$ (500 mg, 3.6 mmol) was added to a solution of the residue in DCM (2 mL) and stirred for 30 min before adding water (0.3 mL) and stirred for 1 h. The mixture was filtered and the filtrate dried ($Na_2SO_4$) and solvents removed in vacuo. The residue was purified by column chromatography (normal phase, 5 g Isolute-Si column, EtOAc in Hexane (1:1) followed by 1-10% MeOH in EtOAc). The residue was dried in vacuo to give (2S)-morpholin-2-ylmethyl 4-phenylpiperazine-1-carboxylate (101 mg, 75%) as a white solid.

Analytical HPLC: purity 98.9% (System B, $R_T$=6.63 min); Analytical LCMS: purity 100% (System B, $R_T$=6.57 min), $ES^+$: 306.7 $[MH]^+$; HRMS calcd for $C_{16}H_{23}N_3O_3$:305.1739, found 305.1753.

Example 12

(2R)-Morpholin-2-ylmethyl 4-phenylpiperazine-1-carboxylate

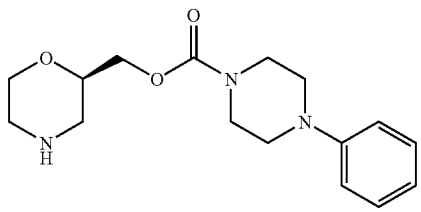

(R)-2-Hydroxymethyl-morpholine-4-carboxylic acid tert-butyl ester (Intermediate 9; 100 mg, 0.46 mmol) was added to a suspension of NaH (60% dispersion in oil; 55.0 mg, 1.38 mmol) in anhydrous THF (5 mL) and stirred under nitrogen for 30 min. 4-Nitrophenyl 4-phenylpiperazine-1-carboxylate (Intermediate 2; 180 mg, 0.55 mmol) was added and the reaction mixture was stirred at room temperature for 48 h. The reaction mixture was filtered through celite and the solid washed with THF (10 mL). The filtrates were combined and the solvent removed in vacuo. The residue was purified by column chromatography (normal phase, silica, 5 g Isolute-Si column, gradient 10% to 50% EtOAc in hexane) to give (2R)-(4-phenylpiperazine-1-carbonyloxymethyl)-morpholine-4-carboxylic acid tert-butyl ester (170 mg, 91%) as a light yellow oil.

(2R)-(4-Phenylpiperazine-1-carbonyloxymethyl)-morpholine-4-carboxylic acid tert-butyl ester (130 mg, 0.32 mmol) was dissolved in DCM (2 mL) and TFA (3 mL, 10% in DCM) was added. The reaction mixture was stirred at room temperature overnight. The solvents were removed in vacuo. Heptane was added and the solvent removed in vacuo. $K_2CO_3$ (500 mg, 3.6 mmol) was added to a solution of the residue in DCM (2 mL) and stirred for 30 min before adding water (0.3 mL) and stirred for 1 h. The mixture was filtered and the filtrate dried ($Na_2SO_4$) and solvents removed in vacuo. The residue was purified by column chromatography (normal phase, 5 g Isolute-Si column, EtOAc in Hexane (1:1) followed by 1-10% MeOH in EtOAc). The residue was dried in vacuo to give (2R)-morpholin-2-ylmethyl 4-phenylpiperazine-1-carboxylate (57 mg, 58%) as a white solid.

Analytical HPLC: purity 99.8% (System B, $R_T$=6.63 min); Analytical LCMS: purity 100% (System B, $R_T$=6.54 min), $ES^+$: 306.7 $[MH]^+$; HRMS calcd for $C_{16}H_{23}N_3O_3$:305.1739, found 305.1753.

Example 13

(4-Methylmorpholin-2-yl)methyl 4-phenylpiperazine-1-carboxylate

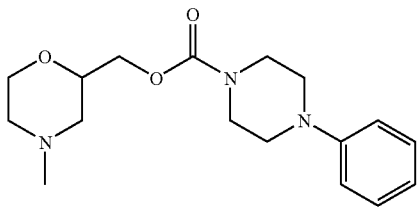

Morpholin-2-ylmethyl 4-phenylpiperazine-1-carboxylate (non-HCl salt of Example 10; 1.00 g, 3.27 mmol) and 37% formaldehyde in water (1.97 g, 1.82 mL, 65.5 mmol) were dissolved in MeOH (20 mL) at room temperature followed by addition of sodium triacetoxyborohydride (2.78 g, 13.1 mmol) portionwise over 5 minutes. The reaction mixture was stirred for 2 h. The reaction mixture was quenched by the addition of saturated aq $Na_2CO_3$ solution. The solvents were removed in vacuo and the residual aqueous phase was loaded onto an Isolute HM-N 20 mL cartridge. The desired product was eluted with DCM (200 mL) and the solvent removed in vacuo to give (4-methylmorpholin-2-yl)methyl 4-phenylpiperazine-1-carboxylate (0.93 g, 88.9%) as a colourless gum.

Analytical HPLC: purity 99.5% (System A, $R_T$=3.64 min); Analytical LCMS: purity 100% (System A, $R_T$=4.01 min), $ES^+$: 320.1 $[MH]^+$; HRMS calcd for $C_{17}H_{25}N_3O_3$:319.1896, found 319.1899.

Example 14

[(2S)-4-Methylmorpholin-2-yl]methyl 4-phenylpiperazine-1-carboxylate

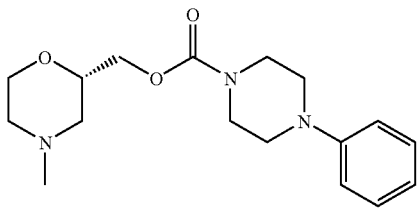

(S)-(4-Methyl-morpholin-2-yl)-methanol (Intermediate 10; 100 mg, 0.76 mmol) was added to a suspension of NaH (60% dispersion in oil; 90.0 mg, 2.28 mmol,) in anhydrous THF (7 mL) and stirred under nitrogen for 30 min. 4-Nitrophenyl 4-phenylpiperazine-1-carboxylate (Intermediate 2; 300 mg, 0.92 mmol) was added and the reaction mixture was stirred at room temperature for 48 h. The reaction mixture was

Example 15

[(2R)-4-Methylmorpholin-2-yl]methyl 4-phenylpiperazine-1-carboxylate

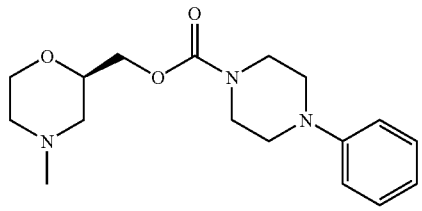

(R)-(4-Methyl-morpholin-2-yl)-methanol (Intermediate 11; 100 mg, 0.76 mmol) was added to a suspension of NaH (60% dispersion in oil; 90.0 mg, 2.28 mmol) in anhydrous THF (7 mL) and stirred under nitrogen for 30 min. 4-Nitrophenyl 4-phenylpiperazine-1-carboxylate (Intermediate 2; 300 mg, 0.92 mmol) was added and the reaction mixture was stirred at room temperature for 48 h. The reaction mixture was filtered through celite and the solid washed with THF (10 mL). The filtrates were combined and the solvent removed in vacuo. The residue was purified by column chromatography (normal phase silica, 5 g Isolute-Si column, gradient 1-5% MeOH in DCM). The solvents were removed in vacuo to give [(2R)-4-methylmorpholin-2-yl]methyl 4-phenylpiperazine-1-carboxylate (175 mg, 72%) as a light yellow gum Analytical HPLC: purity 99.8% (System B, $R_T$=6.84 min); Analytical LCMS: purity 100% (System A, $R_T$=3.67 min), ES$^+$: 320.5 [MH]$^+$; HRMS calcd for $C_{17}H_{25}N_3O_3$:319.1896, found 319.1895.

Example 16

[(2S)-4-Methylmorpholin-2-yl]methyl 4-(4-fluorophenyl)piperazine-1-carboxylate

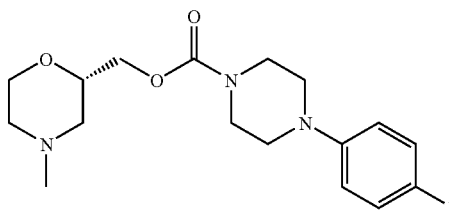

(S)-(4-Methyl-morpholin-2-yl)-methanol (Intermediate 10; 100 mg, 0.76 mmol) was added to a suspension of NaH (60% dispersion in oil; 90.0 mg, 2.28 mmol) in anhydrous THF (7 mL) and stirred under nitrogen for 30 min. 4-(4-Fluorophenyl)-piperazine-1-carboxylic acid 4-nitrophenyl ester (Intermediate 6; 314 mg, 0.91 mmol) was added and the reaction mixture was stirred at room temperature for 48 h. The reaction mixture was filtered through celite and the solid washed with THF (10 mL). The filtrates were combined and the solvent removed in vacuo. The residue was purified by column chromatography (normal phase silica, 5 g Isolute-Si column, gradient 1-5% MeOH in DCM) and the solvents were removed in vacuo to give [(2S)-4-methylmorpholin-2-yl]methyl 4-(4-fluorophenyl)-piperazine-1-carboxylate (130 mg, 51%) as a light brown solid.

Analytical HPLC: purity 96.0% (System B, $R_T$=7.46 min); Analytical LCMS: purity 100% (System A, $R_T$=3.97 min), ES$^+$: 338.6 [MH]$^+$; HRMS calcd for $C_{17}H_{24}FN_3O_3$: 337.1802, found 337.1814.

Example 17

[(2R)-4-Methylmorpholin-2-yl]methyl 4-(4-fluorophenyl)piperazine-1-carboxylate

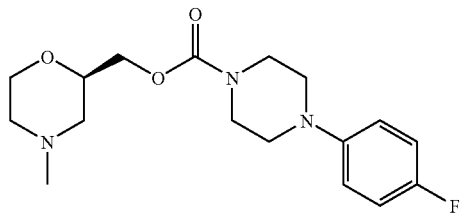

(R)-(4-Methyl-morpholin-2-yl)-methanol (Intermediate 11; 100 mg, 0.76 mmol) was added to a suspension of NaH (60% dispersion in oil; 90.0 mg, 2.28 mmol) in anhydrous THF (7 mL) and stirred under nitrogen for 30 min. 4-(4-Fluorophenyl)-piperazine-1-carboxylic acid 4-nitrophenyl ester (Intermediate 6; 314 mg, 0.91 mmol) was added and the reaction mixture was stirred at room temperature for 48 h. The reaction mixture was filtered through celite and the solid washed with THF (10 mL). The filtrates were combined and the solvent removed in vacuo. The residue was purified by column chromatography (normal phase silica, 5 g Isolute-Si column, gradient 1-5% MeOH in DCM) and then reverse phase HPLC (YMC ODS-A 100×20 mm, 5 μm, 25 mL/min, gradient 20% to 100% (over 7 min) then 100% (3 min) MeOH in 10% MeOH/water). The pure product was taken up in DCM (5 mL), filtered, and dried in vacuo to give [(2R)-4-methylmorpholin-2-yl]methyl 4-(4-fluorophenyl)piperazine-1-carboxylate (100 mg, 28%) as a colourless gum.

Analytical HPLC: purity 99.7% (System A, $R_T$=3.97 min); Analytical LCMS: purity 100% (System A, $R_T$=3.94 min), ES$^+$: 338.3 [MH]$^+$; HRMS calcd for $C_{17}H_{24}FN_3O_3$: 337.1802, found 337.1815.

Example 18

[(2S)-4-Methylmorpholin-2-yl]methyl 4-(2,4-difluorophenyl)piperazine-1-carboxylate

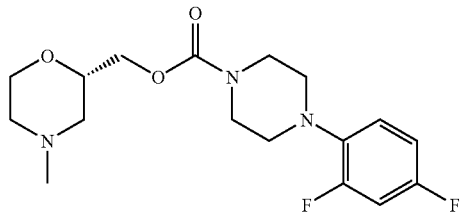

(S)-(4-Methylmorpholin-2-yl)-methanol (Intermediate 10; 100 mg, 0.76 mmol) was added to a suspension of NaH

--- filtered through celite and the solid washed with THF (10 mL). The filtrates were combined and the solvent removed in vacuo. The residue was purified by column chromatography (normal phase silica, 5 g Isolute-Si column, gradient 1-5% MeOH in DCM) then by reverse phase HPLC(YMC ODS-A 100×20 mm, 5 μm, 25 mL/min, gradient 20% to 100% (over 7 min) then 100% (3 min) MeOH in 10% MeOH/water). The pure product was taken up in DCM (5 mL), filtered, and dried in vacuo to give [(2S)-4-methylmorpholin-2-yl]methyl 4-phenyl-piperazine-1-carboxylate (50 mg, 20%) as a colourless gum.

Analytical HPLC: purity 99.4% (System A, $R_T$=3.65 min); Analytical LCMS: purity 100% (System A, $R_T$=3.66 min), ES$^+$: 320.3 [MH]$^+$; HRMS calcd for $C_{17}H_{25}N_3O_3$: 319.1896, found 319.1909.

(60% dispersion in oil; 90.0 mg, 2.28 mmol) in anhydrous THF (7 mL) and stirred under nitrogen for 30 min. 4-(2,4-Difluorophenyl)-piperazine-1-carboxylic acid 4-nitrophenyl ester (Intermediate 12, 330 mg, 0.91 mmol) was added and the reaction mixture was stirred at room temperature for 48 h. The reaction mixture was filtered through celite and the solid washed with THF (10 mL). The filtrates were combined and the solvent removed in vacuo. The residue was purified by column chromatography (normal phase silica, 5 g Isolute-Si column, gradient 1-5% MeOH in DCM) and the solvents were removed in vacuo to give [(2S)-4-methylmorpholin-2-yl]methyl 4-(2,4-difluorophenyl)-piperazine-1-carboxylate (104 mg, 38%) as a colourless gum.

Analytical HPLC: purity 99.3% (System B, $R_T$=8.55 min); Analytical LCMS: purity 100% (System B, $R_T$=8.32 min), ES$^+$: 356.7 [MH]$^+$; HRMS calcd for $C_{17}H_{23}F_2N_3O_3$: 355.1707, found 355.1724.

Example 19

[(2R)-4-Methylmorpholin-2-yl]methyl 4-(2,4-difluorophenyl)piperazine-1-carboxylate

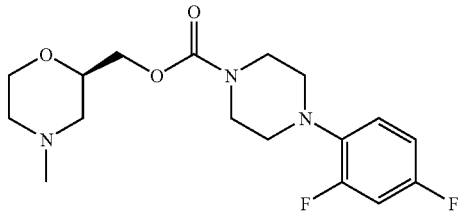

(R)-(4-Methylmorpholin-2-yl)-methanol (Intermediate 11; 100 mg, 0.76 mmol) was added to a suspension of NaH (60% dispersion in oil; 90.0 mg, 2.28 mmol) in anhydrous THF (7 mL) and stirred under nitrogen for 30 min. 4-(2,4-Difluorophenyl)-piperazine-1-carboxylic acid 4-nitrophenyl ester (Intermediate 12; 330 mg, 0.91 mmol) was added and the reaction mixture was stirred at room temperature for 48 h. The reaction mixture was filtered through celite and the solid washed with THF (10 mL). The filtrates were combined and the solvent removed in vacuo. The residue was purified by column chromatography (normal phase silica, 5 g Isolute-Si column, gradient 1-5% MeOH in DCM) and the solvents were removed in vacuo to give [(2R)-4-methylmorpholin-2-yl]methyl 4-(2,4-difluorophenyl)-piperazine-1-carboxylate (87 mg, 32%) as a colourless gum.

Analytical HPLC: purity 100% (System B, $R_T$=8.57 min); Analytical LCMS: purity 100% (System A, $R_T$=4.62 min), ES$^+$: 356.4 [MH]$^+$; HRMS calcd for $C_{17}H_{23}F_2N_3O_3$: 355.1707, found 355.1722.

Example 20

Morpholin-2-ylmethyl 4-(4-fluorophenyl)piperazine-1-carboxylate Dihydrochloride

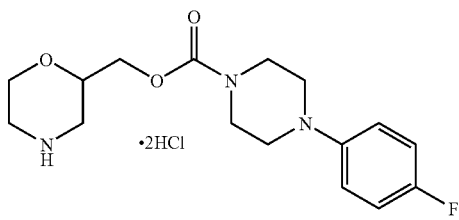

2-Hydroxymethyl-morpholine-4-carboxylic acid tert-butyl ester (2.17 g, 10 mmol) was dissolved in anhydrous THF (50 mL) and the reaction mixture was cooled to 0° C. NaH (60% dispersion in oil; 0.40 g, 10 mmol) was added and stirred for 10 minutes before 4-(4-fluorophenyl)-piperazine-1-carboxylic acid 4-nitrophenyl ester (Intermediate 6; 3.45 g, 10 mmol) was added. The reaction mixture was stirred at room temperature overnight and then cautiously quenched by dropwise addition of water (1 mL)/THF (10 mL) mixture before the THF was removed in vacuo. The residue was suspended between sat aq $Na_2CO_3$ (50 mL) and EtOAc (200 mL). The organic layer was washed with sat aq $Na_2CO_3$ (5×50 mL), dried ($MgSO_4$) and dried in vacuo. The residue was purified by reverse phase column chromatography (LiChroprep RP-18, 40-63 μm, 460×26 mm (100 g), 30 mL/min, gradient 0% to 60% (over 60 min) MeOH in water) to give ~80% pure material by HPLC. The crude intermediate was dissolved in DCM (100 mL) and TFA (10 mL, excess) and was stirred at room temperature overnight. The solvent was removed in vacuo and the residue was repurified by reverse phase column chromatography (LiChroprep RP-18, 40-63 μm, 460×26 mm (100 g), 30 mL/min, gradient 0% to 20% (over 70 min) then held at 20% (over 120 min) MeOH in water with 1% formic acid. The solvent was removed in vacuo and the residue was de-salted using $K_2CO_3$ in DCM. The residue was dissolved in DCM and HCl (2M in $Et_2O$, 3.2 mL, 6.4 mmol), dried in a vacuum oven overnight to give the morpholin-2-ylmethyl 4-(4-fluorophenyl)piperazine-1-carboxylate dihydrochloride salt (2.30 g, 58%) as a colourless gum.

Analytical HPLC: purity 97.5% (System A, $R_T$=3.90 min); Analytical LCMS: purity 100% (System A, $R_T$=4.27 min), ES$^+$: 324.1 [MH]$^+$; HRMS calcd for $C_{16}H_{22}FN_3O_3$: 323.1645, found 323.1660.

Example 21

(2S)-Morpholin-2-ylmethyl 4-(4-fluorophenyl)piperazine-1-carboxylate

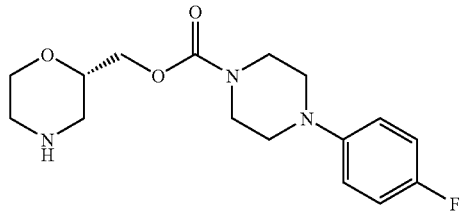

(S)-2-Hydroxymethyl-morpholine-4-carboxylic acid tert-butyl ester (Intermediate 8; 100 mg, 0.46 mmol) was added to a suspension of NaH (60% dispersion in oil; 55.0 mg, 1.38 mmol) in anhydrous THF (2 mL) and stirred under nitrogen for 30 min. 4-(4-Fluorophenyl)-piperazine-1-carboxylic acid 4-nitrophenyl ester (Intermediate 6; 191 mg, 0.55 mmol) was added and the reaction mixture was stirred at room temperature for 48 h. The reaction mixture was filtered through celite and the solid washed with THF (10 mL). The filtrates were combined and the solvent removed in vacuo. The residue was purified by column chromatography (normal phase silica, 5 g Isolute-Si column, gradient 10% to 50% EtOAc in hexane) to give (2S)-[4-(4-fluoro-phenyl)-piperazine-1-carbonyloxymethyl]-morpholine-4-carboxylic acid tert-butyl ester (200 mg, quantitative) as a light yellow oil.

S)-[4-(4-Fluoro-phenyl)-piperazine-1-carbonyloxymethyl]-morpholine-4-carboxylic acid tert-butyl ester (200 mg, 0.46 mmol) was dissolved in DCM (2 mL) and TFA (3 mL, 10% in DCM) was added. The reaction mixture was stirred at room temperature overnight. The solvents were removed in vacuo. Heptane was added and then the solvent was removed in vacuo. K₂CO₃ (500 mg, 3.6 mmol) was added to a solution of the residue in DCM (2 mL) and stirred for 30 min before adding water (0.3 mL) and stirred for 1 h. The mixture was filtered and the filtrate dried (Na₂SO₄) and solvents removed in vacuo. The residue was purified by column chromatography (normal phase, 5 g Isolute-Si column, EtOAc in hexane (1:1) followed by 1-10% MeOH in EtOAc). The residue was dried in vacuo to give (2S)-morpholin-2-ylmethyl 4-(4-fluorophenyl)piperazine-1-carboxylate (135 mg, 89%) as a white solid.

Analytical HPLC: purity 98.2% (System B, $R_T$=7.23 min); Analytical LCMS: purity 100% (System B, $R_T$=7.12 min), ES⁺: 324.7 [MH]⁺; HRMS calcd for $C_{16}H_{22}FN_3O_3$: 323.1645, found 323.1659.

Example 22

(2R)-Morpholin-2-ylmethyl 4-(4-fluorophenyl)piperazine-1-carboxylate

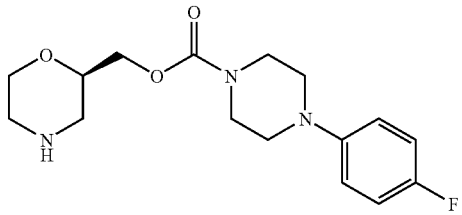

(R)-2-Hydroxymethyl-morpholine-4-carboxylic acid tert-butyl ester (Intermediate 9; 100 mg, 0.46 mmol) was added to a suspension of NaH (60% dispersion in oil; 55.0 mg, 1.38 mmol) in anhydrous THF (2 mL) and stirred under nitrogen for 30 min. 4-(4-Fluorophenyl)-piperazine-1-carboxylic acid 4-nitrophenyl ester (Intermediate 6; 191 mg, 0.55 mmol) was added and the reaction mixture was stirred at room temperature for 48 h. The reaction mixture was filtered through celite and the solid washed with THF (10 mL). The filtrates were combined and the solvent removed in vacuo. The residue was purified by column chromatography (normal phase silica, 5 g Isolute-Si column, gradient 10% to 50% EtOAc in hexane) to give (2R)-[4-(4-fluoro-phenyl)-piperazine-1-carbonyloxymethyl]-morpholine-4-carboxylic acid tert-butyl ester (130 mg, 67%) as a colourless oil.

(2R)-[4-(4-Fluoro-phenyl)-piperazine-1-carbonyloxymethyl]-morpholine-4-carboxylic acid tert-butyl ester (120 mg, 0.40 mmol) was dissolved in DCM (2 mL) and TFA (3 mL, 10% in DCM) was added. The reaction mixture was stirred at room temperature overnight. The solvents were removed in vacuo. Heptane was added and then the solvents were removed in vacuo. K₂CO₃ (500 mg, 3.6 mmol) was added to a solution of the residue in DCM (2 mL) and stirred for 30 min before adding water (0.3 mL) and stirred for 1 h. The mixture was filtered and the filtrate dried (Na₂SO₄) and solvents removed in vacuo. The residue was purified by column chromatography (normal phase, 5 g Isolute-Si column, EtOAc in hexane (1:1) followed by 1-10% MeOH in EtOAc). The residue was dried in vacuo to give (2R)-morpholin-2-ylmethyl 4-(4-fluorophenyl)piperazine-1-carboxylate (117 mg, 91%) as a white solid.

Analytical HPLC: purity 99.3% (System B, $R_T$=7.25 min); Analytical LCMS: purity 97.9% (System B, $R_T$=7.13 min), ES⁺: 324.6 [MH]⁺; HRMS calcd for $C_{16}H_{22}FN_3O_3$: 323.1645, found 323.1659.

Example 23

(4-Methylmorpholin-2-yl)methyl 4-(4-chlorophenyl)piperazine-1-carboxylate Dihydrochloride

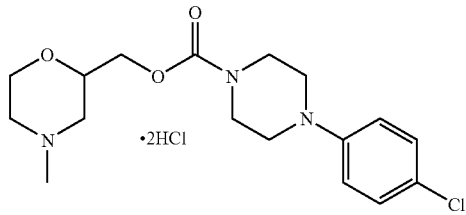

(4-Methyl-morpholin-2-yl)-methanol (1.05 g, 8.0 mmol) and DIPEA (2.79 ml, 16.0 mmol were dissolved in DCM (80 mL) and the reaction mixture was cooled to 0° C. and p-nitrophenyl chloroformate (3.23 g, 16.0 mmol) was added. The reaction mixture was allowed to warm to room temperature and stirred for 2 h. The reaction mixture was divided into 4 batches and concentrated in vacuo. One portion was dissolved in DMF (20 mL) and 1-(4-chlorophenyl)-piperazine dihydrochloride (539 mg, 2 mmol) was added, and the resulting reaction mixture was stirred at room temperature for 24 h. The solvent was removed in vacuo and the residue was dissolved in DCM (30 mL). The organic layer was washed with 1.0M Na₂CO₃ solution (3×30 mL), dried (MgSO₄) and the solvents were removed in vacuo. The residue was purified by column chromatography (normal phase, 20 g, Strata SI-1, silica gigatube, 20 mL/min, gradient 0% to 5% MeOH in DCM, residue dry loaded). The solvents were removed in vacuo and the residue was dissolved in DCM (50 mL), filtered and 2M HCl in Et₂O (2 mL, 4 mmol) added. The solvents were removed in vacuo and the resulting solid was dried in a vacuum oven overnight to give the (4-methylmorpholin-2-yl)methyl 4-(4-chlorophenyl)piperazine-1-carboxylate dihydrochloride salt (0.510 g, 60%) as a white solid.

Analytical HPLC: purity 100% (System A, $R_T$=4.69 min); Analytical LCMS: purity 100% (System A, $R_T$=5.12 min), ES⁺: 354.4 [MH]⁺; HRMS calcd for $C_{17}H_{24}Cl_1N_3O_3$: 353.1506, found 353.1516.

Example 24

(4-Methylmorpholin-2-yl)methyl 4-(4-fluorobenzyl)piperazine-1-carboxylate Dihydrochloride

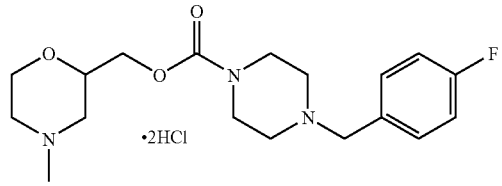

(4-Methyl-morpholin-2-yl)-methanol (1.05 g, 8.0 mmol) and DIPEA (2.79 ml, 16.0 mmol were dissolved in DCM (80 mL) and the reaction mixture was cooled to 0° C. and p-nitrophenyl chloroformate (3.23 g, 16.0 mmol) was added. The reaction mixture was allowed to warm to room temperature and stirred for 2 h. The reaction mixture was divided into 4 batches and concentrated in vacuo. One portion was dissolved in DMF (20 mL) and 1-(4-fluoro-benzyl)-piperazine (0.39 g, 2 mmol) added and the resulting reaction mixture stirred at room temperature for 24 h. The solvent was removed in vacuo and the residue was taken up in DCM (30 mL). The organic layer was washed with 1.0M Na$_2$CO$_3$ solution (3×30 mL), dried (MgSO$_4$) and the solvents were removed in vacuo. The residue was purified by column chromatography (normal phase, 20 g, Strata SI-1, silica gigatube, 20 mL/min, gradient 0% to 5% MeOH in DCM, residue dry loaded). The solvents were removed in vacuo and the residue was dissolved in DCM (50 mL), filtered and 2M HCl in Et$_2$O (2 mL, 4 mmol) added. The solvent was removed in vacuo and the residue was dried in a vacuum oven overnight to give the (4-methylmorpholin-2-yl)methyl 4-(4-fluorobenzyl)piperazine-1-carboxylate dihydrochloride salt (0.375 g, 44%) as a white solid.

Analytical HPLC: purity 99.2% (System A, R$_T$=3.13 min); Analytical LCMS: purity 100% (System A, R$_T$=3.60 min), ES$^+$: 352.5 [MH]$^+$.

Example 25

(4-Acetylmorpholin-2-yl)methyl 4-phenylpiperazine-1-carboxylate

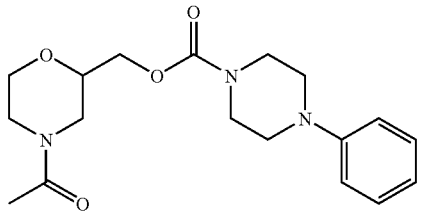

To a stirred solution of morpholin-2-ylmethyl 4-phenylpiperazine-1-carboxylate dihydrochloride (Example 10; 0.52 g, 1.40 mmol) in pyridine (2.25 mL, 27.7 mmol) was slowly added acetyl chloride (0.15 mL, 2.10 mmol). The reaction mixture was stirred at room temperature for 1 h before the pyridine was removed in vacuo and the resulting residue diluted with sat aq NaHCO$_3$ solution (50 mL). The organic product was extracted with EtOAc (3×50 mL). The combined organic layers were washed with sat aq NaHCO$_3$ solution (3×50 mL), dried (MgSO$_4$) and the solvent removed in vacuo. The residue was purified by column chromatography (normal phase, 20 g, Strata SI-1, silica gigatube, 20 mL/min, gradient 0% to 5% MeOH in EtOAc). The solvents were removed in vacuo and dried in a vacuum oven overnight to afford (4-acetylmorpholin-2-yl)methyl 4-phenylpiperazine-1-carboxylate (0.38 g, 78%) as a pale brown oil.

Analytical HPLC: purity 99.0% (System A, R$_T$=4.34 min); Analytical LCMS: purity 100% (System A, R$_T$=4.60 min), ES$^+$: 348.5 [MH]$^+$; HRMS calcd for C$_{18}$H$_{25}$N$_3$O$_4$:347.1845, found 347.1859.

Example 26

Morpholin-3-ylmethyl 4-(4-fluorophenyl)piperazine-1-carboxylate

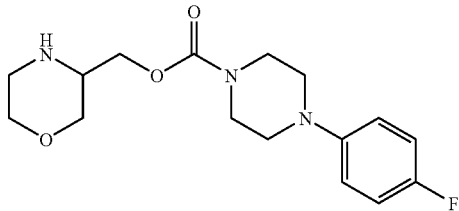

NaH (60% in oil, prewashed with hexane; 1.30 g, 31.7 mmol) was suspended in anhydrous THF (50 mL) under nitrogen and the reaction mixture was cooled to −10° C. with stirring. A solution of 3-hydroxymethyl-morpholine-4-carboxylic acid tert-butyl ester (Intermediate 7; 2.30 g, 10.6 mmol) in THF (50 mL) was added dropwise. The reaction mixture was stirred for 20 min at 0° C. 4-(4-Fluorophenyl)-piperazine-1-carboxylic acid 4-nitrophenyl ester (Intermediate 6; 4.38 g, 12.7 mmol) was added and the reaction mixture was stirred overnight at room temperature. Sat aq NaHCO$_3$ solution (10 mL) was added and the solvents were removed in vacuo. The residue was partitioned between water and EtOAc and the aqueous phase extracted with EtOAc. The combined organic extracts were washed with sat aq NaHCO$_3$ (3×100 mL), dried (MgSO$_4$) and the solvent removed in vacuo. The residue was purified by flash normal column chromatography (Apollo silica, 40-63 µm, 60 A) eluting with EtOAc/hexane. Impure material was further purified by flash normal phase chromatography using 1% MeOH in DCM to give 3-[4-(4-fluorophenyl)-piperazine-1-carbonyloxymethyl]-morpholine-4-carboxylic acid tert-butyl ester (3.05 g, 68%).

3-[4-(4-Fluorophenyl)-piperazine-1-carbonyloxymethyl]-morpholine-4-carboxylic acid tert-butyl ester (2.98 g, 7.04 mmol) was stirred in DCM (30 mL) at 0° C. TFA (6 mL) dissolved in DCM (24 mL) was added dropwise. The reaction mixture was stirred overnight at room temperature. The solvent was removed in vacuo and the residue was partitioned between DCM (30 mL) and aqueous NaHCO$_3$ (5 g in 30 mL). The aqueous layer was extracted with DCM (3×30 mL), dried (MgSO$_4$) and the solvent removed in vacuo to give morpholin-3-ylmethyl 4-(4-fluorophenyl)piperazine-1-carboxylate (2.18 g, 96%) as a white solid.

Analytical HPLC: purity 98.3% (System A, R$_T$=3.88 min); Analytical LCMS: purity 100% (System A, R$_T$=4.27 min), ES$^+$: 324.0 [MH]$^+$; HRMS calcd for C$_{16}$H$_{22}$FN$_3$O$_3$: 323.1645, found 323.1661.

Example 27

(3S)-Morpholin-3-ylmethyl 4-(4-fluorophenyl)piperazine-1-carboxylate

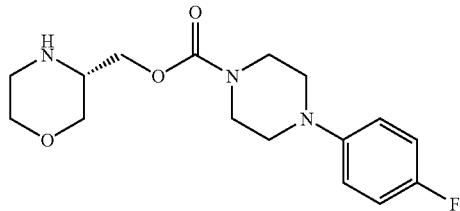

NaH (60% in oil, prewashed with hexane; 2.76 g, 69.0 mmol) was suspended in anhydrous THF (100 mL) under nitrogen and the reaction mixture was cooled to 0° C. with stirring. A solution of (S)-3-hydroxymethyl-morpholine-4-carboxylic acid tert-butyl ester (5.00 g, 23.0 mmol) in THF (100 mL) was added dropwise. The reaction mixture was stirred for 30 minutes at 0° C. 4-(4-Fluorophenyl)-piperazine-1-carboxylic acid 4-nitrophenyl ester (Intermediate 6; 10.0 g, 29.0 mmol) was added and the reaction mixture was stirred overnight at room temperature before standing for 24 h. The reaction mixture was cooled to 5-10° C. A 10% aqueous solution of NaHCO$_3$ (22 mL) was added and the solvents were removed in vacuo. The residue was partitioned between EtOAc (700 mL) and 10% aqueous solution of NaHCO$_3$ (200 mL)/water (400 mL). The EtOAc layer was dried (MgSO$_4$) and the solvent removed in vacuo. The residue was purified by column chromatography (normal phase silica, 100 g Isolute-Si column, gradient of EtOAc in hexane). The residue was dissolved in DCM and evaporated in vacuo and repeated before drying in vacuo to give (3S)-3-[4-(4-fluorophenyl)- piperazine-1-carbonyloxymethyl]-morpholine-4-carboxylic acid tert-butyl ester (8.19 g, 84%) as an orange gum.

S)-3-[4-(4-Fluorophenyl)-piperazine-1-carbonyloxymethyl]-morpholine-4-carboxylic acid tert-butyl ester (8.19 g, 19.3 mmol) was stirred in DCM (96 mL) at −5 to 0° C. TFA (28.9 mL) dissolved in DCM (67 mL) was added dropwise and the cooling maintained for 30 minutes. The reaction mixture was stirred for 20 h at room temperature. The reaction mixture was diluted with heptane (200 mL) and a red-brown gum separated. The gum was dried in vacuo and then washed with heptane (200 mL). The residue was partitioned between DCM (450 mL) and 1.2M aqueous $NaHCO_3$ (135 mL). The aqueous layer was extracted with DCM (2×225 mL). The combined DCM extracts were dried ($Na_2SO_4$) and the solvent removed in vacuo to give (3S)-morpholin-3-ylmethyl 4-(4-fluorophenyl)-piperazine-1-carboxylate (5.83 g, 93%) as a beige solid.

Analytical HPLC: purity 99.5% (System A, $R_T$=3.86 min); Analytical LCMS: purity 100% (System A, $R_T$=3.82 min), $ES^+$: 324.7 $[MH]^+$; HRMS calcd for $C_{16}H_{22}FN_3O_3$: 323.1645, found 323.1652.

Example 28

(3R)-Morpholin-3-ylmethyl 4-(4-fluorophenyl)piperazine-1-carboxylate

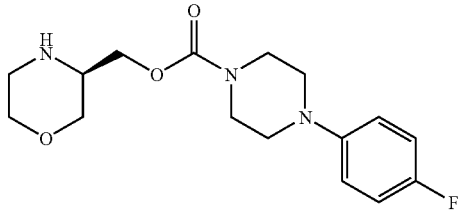

NaH (60% in oil, prewashed with hexane; 1.38 g, 34.5 mmol) was suspended in anhydrous THF (50 mL) under nitrogen, the reaction mixture cooled to −5° C. with stirring and a solution of (R)-3-hydroxymethyl-morpholine-4-carboxylic acid tert-butyl ester (2.50 g, 11.5 mmol) in THF (50 mL) was added dropwise. The reaction mixture was stirred for 30 min at 0 to 3° C. 4-(4-Fluorophenyl)-piperazine-1-carboxylic acid 4-nitrophenyl ester (Intermediate 6; 5.01 g, 14.5 mmol) was added and the reaction mixture was stirred overnight at room temperature. The reaction mixture was cooled with an ice bath and a 10% aq $NaHCO_3$ solution (11 mL) was added. The solvents were removed in vacuo and the residue was partitioned between EtOAc (350 mL) and 10% aq $NaHCO_3$ solution (100 mL)/water (200 mL). The EtOAc layer was dried ($MgSO_4$) and the solvent removed in vacuo. The residue was purified by column chromatography (normal phase silica, 70 g Isolute-Si column, gradient of EtOAc in hexane). The residue was dissolved in DCM and evaporated in vacuo and repeated once before drying in vacuo to give (3R)-3-[4-(4-fluorophenyl)-piperazine-1-carbonyloxymethyl]-morpholine-4-carboxylic acid tert-butyl ester (2.80 g) as a pale yellow gum.

This procedure was repeated on a further batch of (R)-3-hydroxymethyl-morpholine-4-carboxylic acid tert-butyl ester (2.50 g, 11.5 mmol). After repurification of the impure fractions from both batches, 8.17 g (83.9%) of (3R)-3-[4-(4-fluorophenyl)-piperazine-1-carbonyloxymethyl]-morpholine-4-carboxylic acid tert-butyl ester was obtained.

(3R)-3-[4-(4-Fluorophenyl)-piperazine-1-carbonyloxymethyl]-morpholine-4-carboxylic acid tert-butyl ester (5.07 g, 12.0 mmol) was stirred in dry dioxane (35 mL) at room temperature and HCl in dioxane (4M; 15 mL, 60 mmol) was added dropwise. The reaction mixture was stirred for 24 h at room temperature. A further portion of HCl in dioxane (4M; 10 mL, 40 mmol) was added and stirred overnight. The dioxane was decanted and the residual gum was washed with dioxane (×3) and $Et_2O$ (×2). The residue was partitioned between DCM (300 mL) and 1.2M aqueous $NaHCO_3$. The aqueous layer was extracted with DCM (2×200 mL). The combined DCM extracts were dried ($Na_2SO_4$) and the solvent removed in vacuo. The residue was dissolved in DCM and dried in vacuo to give (3R)-morpholin-3-ylmethyl 4-(4-fluorophenyl)piperazine-1-carboxylate (3.87 g, quant.) as an off white solid.

Analytical HPLC: purity 100% (System A, $R_T$=3.87 min); Analytical LCMS: purity 100% (System A, $R_T$=3.82 min), $ES^+$: 324.7 $[MH]^+$; HRMS calcd for $C_{16}H_{22}FN_3O_3$: 323.1645, found 323.1657.

Example 29

(4-Methylmorpholin-3-yl)methyl 4-(4-fluorophenyl)piperazine-1-carboxylate

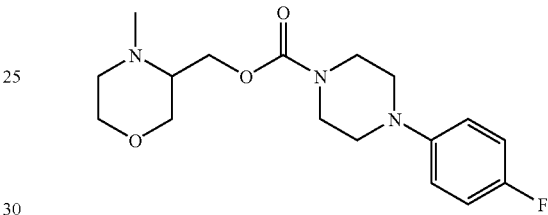

$LiAlH_4$ (4.2 g, 110 mmol) was suspended in anhydrous THF (60 mL) under nitrogen, cooled to −10° C. with stirring and a solution of 3-hydroxymethyl-morpholine-4-carboxylic acid tert-butyl ester (Intermediate 7; 4.1 g, 18.4 mmol) in THF (50 mL) was added dropwise. The reaction mixture was stirred for 20 minutes at 0° C., heated to reflux for 3 h and then stirred at room temperature overnight. The reaction mixture was cooled to −10° C. and quenched with the dropwise addition of 10% water in THF. The reaction mixture was diluted with THF (50 mL), stirred for 1 h at room temperature, filtered and the filtrate was concentrated in vacuo. The residue was dissolved in DCM, dried ($MgSO_4$) and the solvent removed in vacuo to give (4-methyl-morpholin-3-yl)-methanol (2.05 g, 85%) as a colourless liquid.

NaH (60% in oil, prewashed with hexane; 0.91 g, 22.9 mmol) was suspended in anhydrous THF (25 mL) under nitrogen and cooled to 0° C. with stirring. A solution of (4-methyl-morpholin-3-yl)-methanol (1.00 g, 2.62 mmol) in THF (25 mL) was added dropwise. 4-(4-Fluorophenyl)-piperazine-1-carboxylic acid 4-nitrophenyl ester (Intermediate 6; 3.16 g, 9.15 mmol) was added and the reaction mixture was stirred overnight at room temperature. A saturated aqueous solution of $NaHCO_3$ (10 mL) was added and the solvents were removed in vacuo. The residue was partitioned between water and EtOAc and the aqueous phase was extracted with EtOAc. The combined organic extracts were washed with sat aq $NaHCO_3$ (3×100 mL), dried ($MgSO_4$) and the solvents were removed in vacuo. The residue was purified by flash normal column chromatography (Apollo silica, 40-63 μm, 60 Å) eluting with 1% MeOH in DCM to give (4-methylmorpholin-3-yl)methyl 4-(4-fluorophenyl)piperazine-1-carboxylate (2.15 g, 83%) as a white solid.

Analytical HPLC: purity 100% (System A, $R_T$=3.99 min); Analytical LCMS: purity 100% (System A, $R_T$=4.38 min), $ES^+$: 338.0 $[MH]^+$; HRMS calcd for $C_{17}H_{24}FN_3O_3$: 337.1802, found 337.1811.

Example 30

Morpholin-3-ylmethyl 4-phenylpiperazine-1-carboxylate

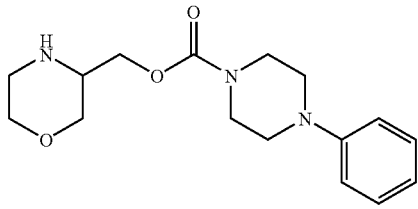

NaH (60% in oil, prewashed with hexane; 1.23 g, 30.1 mmol) was suspended in anhydrous THF (50 mL) under nitrogen and cooled to 0° C. with stirring. A solution of 3-hydroxymethyl-morpholine-4-carboxylic acid tert-butyl ester (Intermediate 7; 2.23 g, 10.3 mmol) in THF (50 mL) was added dropwise. The reaction mixture was stirred for 20 min at 0° C. 4-Nitrophenyl 4-phenylpiperazine-1-carboxylate (Intermediate 2; 4.03 g, 12.3 mmol) was added and the reaction mixture was stirred for 48 h at room temperature. A sat aq NaHCO$_3$ solution (10 mL) was added and the solvents were removed in vacuo. The residue was partitioned between water and EtOAc, the aqueous phase was extracted with EtOAc (2×100 mL). The combined organic extracts were washed with sat aq NaHCO$_3$ (3×100 mL), dried (MgSO$_4$) and the solvents were removed in vacuo. The residue was purified by flash normal column chromatography (Apollo silica, 40-63 μm, 60 A) eluting with 1% MeOH in DCM to give 3-(4-phenyl-piperazine-1-carbonyloxymethyl)-morpholine-4-carboxylic acid tert-butyl ester (3.35 g, 80%).

3-(4-Phenyl-piperazine-1-carbonyloxymethyl)-morpholine-4-carboxylic acid tert-butyl ester (3.31 g, 8.16 mmol) was stirred in DCM (30 mL) at 0° C. TFA (6 mL) dissolved in DCM (24 mL) was added dropwise. The reaction mixture was stirred overnight at room temperature. The solvents were removed in vacuo and the residue was partitioned between DCM (30 mL) and aq NaHCO$_3$ (5 g in 30 mL). The aqueous layer was extracted with DCM (3×30 mL), dried (MgSO$_4$) and the solvents were removed in vacuo to give morpholin-3-ylmethyl 4-phenylpiperazine-1-carboxylate (2.55 g, quant.) as a white solid.

Analytical HPLC: purity 100% (System A, $R_T$=3.60 min); Analytical LCMS: purity 100% (System A, $R_T$=3.97 min), ES$^+$: 306.0 [MH]$^+$; HRMS calcd for $C_{16}H_{23}N_3O_3$: 305.1739, found 305.1741.

Example 31

Morpholin-3-ylmethyl 4-(2,4-difluorophenyl)piperazine-1-carboxylate

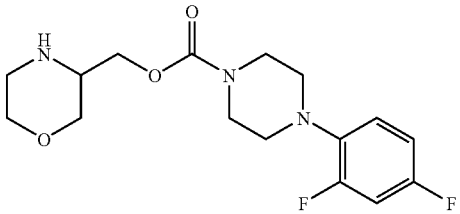

3-Hydroxymethyl-morpholine-4-carboxylic acid tert-butyl ester (Intermediate 7; 250 mg, 0.76 mmol) in THF (5 mL) was added dropwise to a suspension of NaH (60% dispersion in oil, prewashed with hexane; 138 mg, 3.45 mmol) in anhydrous THF (5 mL) at 0° C. and stirred under nitrogen for 35 minutes. 4-(2,4-Difluorophenyl)-piperazine-1-carboxylic acid 4-nitrophenyl ester (Intermediate 12; 501 mg, 1.38 mmol) was added and the reaction mixture was stirred at room temperature overnight. The reaction mixture was quenched with the addition of aqueous NaHCO$_3$ (0.5 mL) at 0° C. and the solvents removed in vacuo. The residue was suspended between aq Na$_2$CO$_3$ (20 mL) and EtOAc (20 mL). The aqueous phase was extracted with EtOAc (2×20 mL). The combined organic layers were washed with aq Na$_2$CO$_3$ (20 mL), dried (MgSO$_4$) and the solvent removed in vacuo. The residue was purified by column chromatography (normal phase, Apollo silica, 1% MeOH in DCM) and the solvents were removed in vacuo to give 3-[4-(2,4-difluoro-phenyl)-piperazine-1-carbonyloxymethyl]-morpholine-4-carboxylic acid tert-butyl ester (170 mg, 34%).

To 3-[4-(2,4-difluoro-phenyl)-piperazine-1-carbonyloxymethyl]-morpholine-4-carboxylic acid tert-butyl ester (170 mg, 0.39 mmol) in DCM (5 mL) at 0° C. was added TFA (1 mL in 5 mL DCM). The reaction mixture was allowed to warm to room temperature and stirred overnight. The solvent was removed in vacuo and the residue suspended between sat aq NaHCO$_3$ (10 mL) and DCM (10 mL). The aqueous phase was extracted with DCM (2×10 mL). The combined organic layers were dried (MgSO$_4$) and the solvent removed in vacuo to give morpholin-3-ylmethyl 4-(2,4-difluorophenyl)piperazine-1-carboxylate (104 mg, 79%) as a colourless oil.

Analytical HPLC: purity 98.7% (System B, $R_T$=8.29 min); Analytical LCMS: purity 100% (System B, $R_T$=8.09 min), ES$^+$: 342.6 [MH]$^+$; HRMS calcd for $C_{16}H_{21}F_2N_3O_3$: 341.1551, found 341.1561.

Example 32

(4-Methylmorpholin-3-yl)methyl 4-(2,4-difluorophenyl)piperazine-1-carboxylate

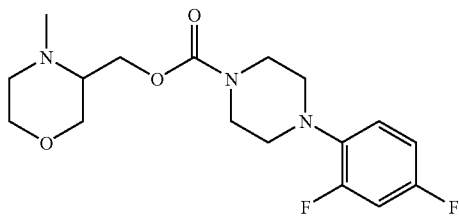

(4-Methyl-morpholin-3-yl)-methanol (387 mg, 2.95 mmol) in THF (7.5 mL) was added dropwise to a suspension of NaH (60% dispersion in oil, prewashed with hexane; 354 mg, 8.85 mmol) in anhydrous THF (7.5 mL) at 0° C. and stirred under nitrogen for 40 minutes. 4-(2,4-Difluorophenyl)-piperazine-1-carboxylic acid 4-nitrophenyl ester (Intermediate 12; 1.28 g, 3.54 mmol) was added and the reaction mixture was stirred at room temperature overnight. The reaction mixture was quenched with the addition of aqueous NaHCO$_3$ (0.5 mL) at 0° C. The reaction mixture was stirred for 1 h and then the solvents were removed in vacuo. The residue was suspended between water and EtOAc. The aqueous phase was extracted with EtOAc (×3). The combined organic layers were washed with aqueous Na$_2$CO$_3$, dried (MgSO$_4$) and the solvent removed in vacuo. The residue was purified by column chromatography (normal phase, Apollo silica, 1% MeOH in DCM) and the solvents were removed in vacuo to give (4-methylmorpholin-3-yl)methyl 4-(2,4-difluorophenyl)piperazine-1-carboxylate (197 mg, 19%) as a colourless oil.

Analytical HPLC: purity 99.3% (System B, $R_T$=8.45 min); Analytical LCMS: purity 100% (System A, $R_T$=4.61 min), ES$^+$: 356.5 [MH]$^+$; HRMS calcd for $C_{17}H_{23}F_2N_3O_3$: 355.1707, found 355.1724.

Example 33

(2S)-Morpholin-2-ylmethyl 4-(2,4-difluorophenyl)piperazine-1-carboxylate

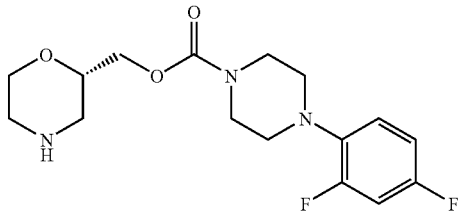

(S)-2-Hydroxymethyl-morpholine-4-carboxylic acid tert-butyl ester (Intermediate 8; 100 mg, 0.46 mmol) was added to a suspension of NaH (60% dispersion in oil; 55.0 mg, 1.38 mmol) in anhydrous THF (2 mL) and stirred under nitrogen for 30 min. 4-(2,4-Difluoro-phenyl)-piperazine-1-carboxylic acid 4-nitrophenyl ester (Intermediate 12; 191 mg, 0.55 mmol) was added and the reaction mixture was stirred at room temperature for 24 h. The reaction mixture was filtered through celite and the solid washed with THF (10 mL). The filtrates were combined and the solvent removed in vacuo. The residue was purified by column chromatography (normal phase silica, 5 g Isolute-Si column, gradient 10% to 50% EtOAc in hexane) to give (2S)-[4-(2,4-difluoro-phenyl)-piperazine-1-carbonyloxymethyl]-morpholine-4-carboxylic acid tert-butyl ester (210 mg, quant.) as an oil.

(2S)-[4-(2,4-Difluoro-phenyl)-piperazine-1-carbonyloxymethyl]-morpholine-4-carboxylic acid tert-butyl ester (205 mg, 0.46 mmol) was dissolved in DCM (2 mL) and TFA (3 mL, 10% in DCM) was added. The reaction mixture was stirred at room temperature overnight. The solvents were removed in vacuo. Heptane was added and the solvent was then removed in vacuo. $K_2CO_3$ (500 mg, 3.6 mmol) was added to a solution of the residue in DCM (2 mL) and stirred for 1 h. The mixture was filtered and the filtrate dried ($Na_2SO_4$) and solvents removed in vacuo. The residue was purified by column chromatography (normal phase, 5 g, Isolute-Si, EtOAc in hexane (1:1) followed by 1-10% MeOH in EtOAc). The residue was dried in vacuo to give (2S)-morpholin-2-ylmethyl 4-(2,4-difluorophenyl)piperazine-1-carboxylate (104 mg, 69%) as a white solid.

Analytical HPLC: purity 99.8% (System B, $R_T$=8.40 min); Analytical LCMS: purity 100% (System B, $R_T$=8.15 min), ES$^+$: 342.6 [MH]$^+$; HRMS calcd for $C_{16}H_{21}F_2N_3O_3$: 341.1551, found 341.1559.

Example 34

(2R)-Morpholin-2-ylmethyl 4-(2,4-difluorophenyl)piperazine-1-carboxylate

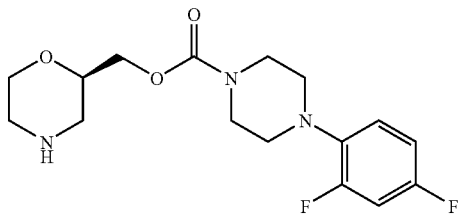

(R)-2-Hydroxymethyl-morpholine-4-carboxylic acid tert-butyl ester (Intermediate 9; 100 mg, 0.46 mmol) was added to a suspension of NaH (60% dispersion in oil; 55.0 mg, 1.38 mmol) in anhydrous THF (2 mL) and stirred under nitrogen for 30 min. 4-(2,4-difluorophenyl)-piperazine-1-carboxylic acid 4-nitrophenyl ester (Intermediate 12; 191 mg, 0.55 mmol) was added and the reaction mixture was stirred at room temperature for 24 h. The reaction mixture was filtered through celite and the solid washed with THF (10 mL). The filtrates were combined and the solvent removed in vacuo. The residue was purified by column chromatography (normal phase silica, 5 g Isolute-Si column, gradient 10% to 50% EtOAc in hexane) to give (2R)-[4-(2,4-difluoro-phenyl)-piperazine-1-carbonyloxymethyl]-morpholine-4-carboxylic acid tert-butyl ester (176 mg, 86%).

(2R)-[4-(2,4-difluoro-phenyl)-piperazine-1-carbonyloxymethyl]-morpholine-4-carboxylic acid tert-butyl ester (176 mg, 0.40 mmol) was dissolved in DCM (2 mL) and TFA (3 mL, 10% in DCM) was added. The reaction mixture was stirred at room temperature overnight. The solvents were removed in vacuo. Heptane was added and then the solvent removed in vacuo. $K_2CO_3$ (500 mg, 3.6 mmol) was added to a solution of the residue in DCM (2 mL) and stirred for 30 min before adding water (0.3 mL) and stirred for 1 h. The mixture was filtered and the filtrate dried ($Na_2SO_4$) and solvents removed in vacuo. The residue was purified by column chromatography (normal phase, 5 g Isolute-Si column, EtOAc in hexane (1:1) followed by 1-10% MeOH in EtOAc). The residue was dried in vacuo to give (2R)-morpholin-2-ylmethyl 4-(2,4-difluorophenyl)piperazine-1-carboxylate (89 mg, 65%) as a white solid.

Analytical HPLC: purity 99.8% (System B, $R_T$=8.38 min); Analytical LCMS: purity 100% (System B, $R_T$=8.23 min), ES$^+$: 342.6 [MH]$^+$; HRMS calcd for $C_{16}H_{21}F_2N_3O_3$: 341.1551, found 341.1561.

Example 35

[(2R)-1,4-Dimethylpiperazin-2-yl]methyl 4-(4-fluorophenyl)piperazine-1-carboxylate

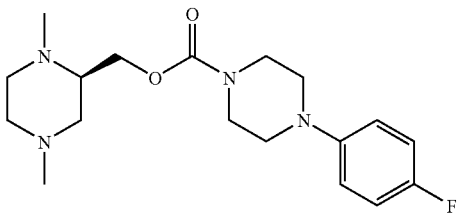

NaH (60% dispersion in mineral oil; 0.45 g, 11.3 mmol) was suspended in anhydrous THF (20 mL) under nitrogen and the reaction mixture was cooled to 0° C. with stirring. A solution of 1,4-dimethyl-(R)-2-hydroxymethyl piperazine (Intermediate 4; 0.50 g, 3.47 mmol) in THF (20 mL) was added dropwise. The reaction mixture was stirred for 10 minutes at 0° C. 4-(4-Fluorophenyl)-piperazine-1-carboxylic acid 4-nitrophenyl ester (Intermediate 6; 1.50 g, 4.34 mmol) was added and the reaction mixture was stirred overnight at room temperature. The reaction mixture was quenched with sat. aq. NaHCO$_3$ (40 mL) and the THF was removed in vacuo. The aqueous phase was extracted with EtOAc (100 mL). The organic layer was washed with sat. aq. NaHCO$_3$ (5×100 mL), dried (MgSO$_4$) and the solvent removed in vacuo. The residue was purified by reverse phase column chromatography (Li-Chroprep RP-18, 40-63 μm, 460×26 mm (100 g), 30 mL/min, gradient 0% to 30% (over 75 min) to 100% (over 13 min) MeOH in water with 1% formic acid). The residue was desalted using K$_2$CO$_3$ in DCM to give [(2R)-1,4-dimethylpiperazin-2-yl]methyl 4-(4-fluorophenyl)piperazine-1-carboxylate (0.42 g, 35%) as a colourless gum.

Analytical HPLC: purity 100% (System A, $R_T$=3.88 min); Analytical LCMS: purity 100% (System A, $R_T$=3.58 min), ES$^+$: 351.2 [MH]$^+$; HRMS calcd for $C_{18}H_{27}FN_4O_2$: 350.2118, found 350.2125.

Biological Methods

Animal Model of Human Obesity (Dietary-Induced Obese Rat)

Rodent models of obesity are valuable tools for studying the underlying factors that contribute to the initiation and maintenance of the obese state in humans. The model of diet-induced obesity (DIO) in rodents is particularly suited to this task as DIO rats share a number of traits with human obesity.

These include polygenic inheritance, insulin resistance, hyperleptinemia, lowered growth hormone secretion, proclivity to preferentially oxidize carbohydrate over fat, and the ability to decrease metabolic rate when calorie-restricted, leading to weight regain after restriction. In outbred rats fed a high energy diet, about one-half develop DIO, while the rest are resistant to obesity and gain no more weight than chow-fed controls (diet resistant, DR). The model of diet-induced obesity (DIO) is of special interest with regard to regulation of energy homeostasis. When fed a diet moderately high in fat, sucrose, and energy content (HE diet), about one-half of the rats will put on substantially more weight than the others (DIO vs. DR).

Rats predisposed to develop DIO will gain weight at rates comparable to rats fed a low-energy (chow) diet and will not become obese unless fed an HE diet. However, once the DIO and DR phenotypes are established on a HE diet, the resulting weight gains and body composition changes persist, even when animals are switched back to a normal chow diet. Changes in body weight and composition, which occur during the development and perpetuation of the DIO and DR phenotypes, are associated with several alterations in brain function that may underlie these adjustments DIO Protocol The diet-induced obesity protocol as described by Widdowson, P. S. et al. (Diabetes (1997) 46:1782-1785) was followed for selection of obese-prone animals.

Wistar male rats (~200-250 g at start of modified dietary intervention) are put on a high-carbohydrate (HE) diet for 8-10 weeks. The composition of the diet is 33% (w/v) powdered chow (RM1), 33% (w/v) condensed milk (Nestle), 7% (w/v) Castor sugar (Tate & Lyle), and 27% (w/v) water. Body weights are recorded and following an 8-week period, animals are separated in 2 groups according to their weight. As in any outbred strain of animals (rodents, primates) a population will naturally separate in two groups: individuals prone to obesity (putting on more weight) or obesity-resistant (putting on less weight). The obese animals weigh up to 60 g more after 6 weeks. Obese-prone animals are kept to perform studies on the effect on body weight and food intake of compounds of formula (I). FIG. 1 shows an example of body weight separation between animals fed on the highly palatable diet (high carbohydrate).

In Vivo Experiments on the Effect of the Compounds on Body Weight

Figure 2:
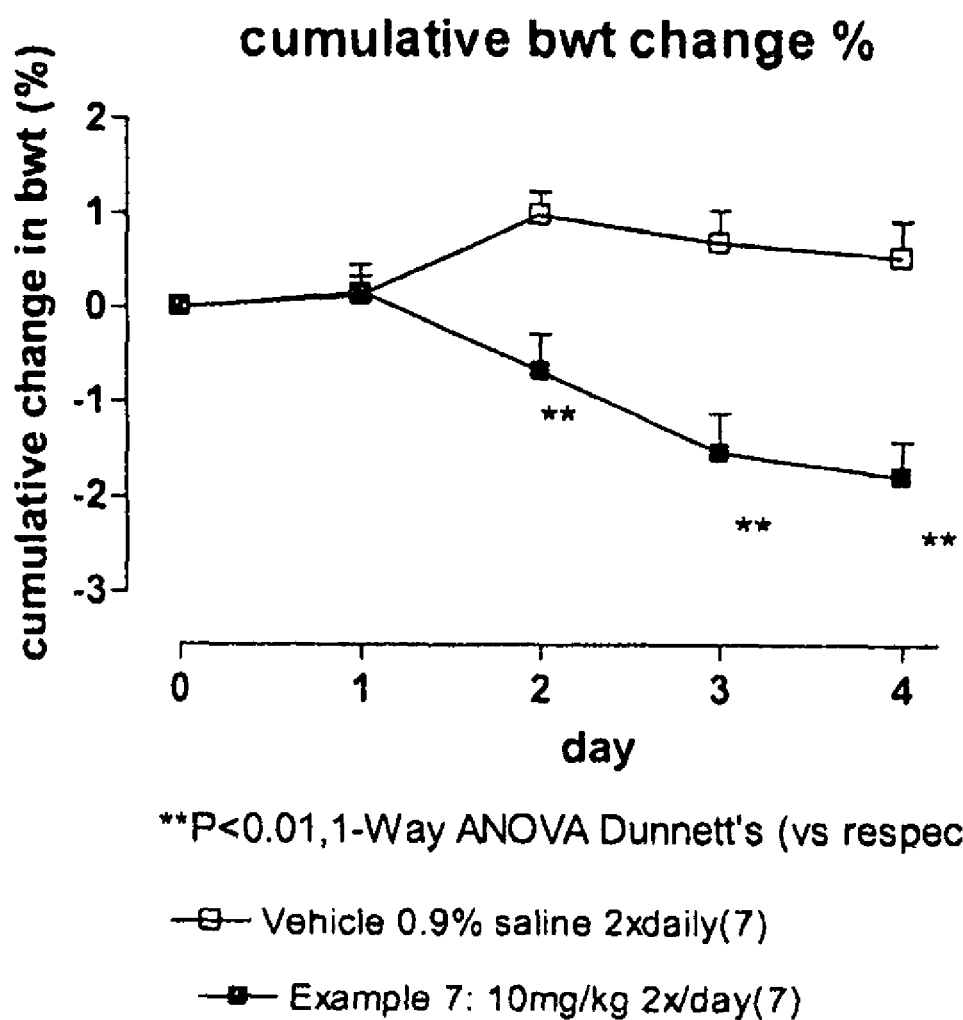
FIG. 2 shows the cumulative body weight change (%) observed in a 4 day study in DIO rats for Example 7.
Figure 3:
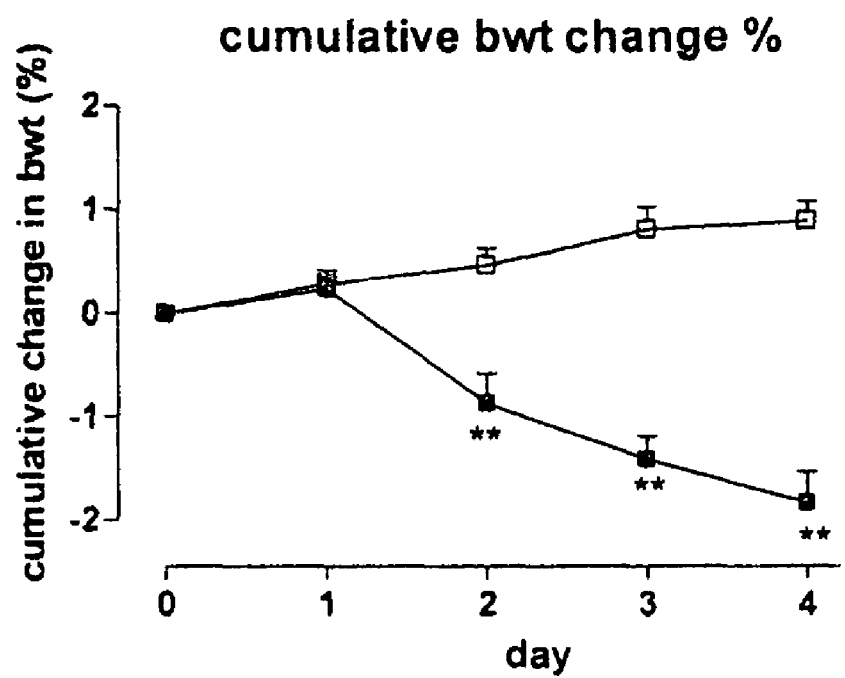
FIG. 3 shows the cumulative body weight change (%) observed in a 4 day study in DIO rats for Example 20.
Figure 4:
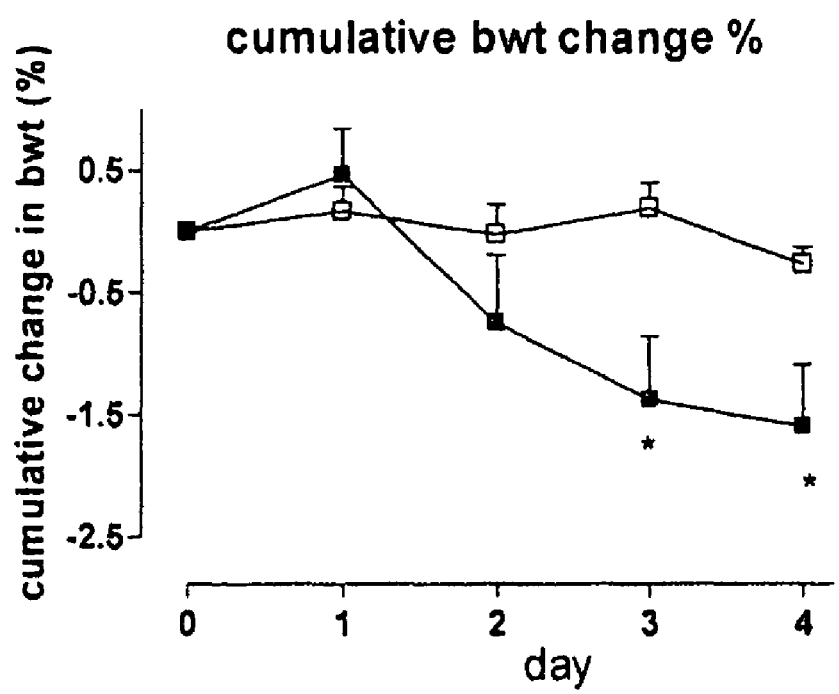
FIG. 4 shows the cumulative body weight change (%) observed in a 4 day study in DIO rats for Example 30.

Obese-prone animals are treated with a compound of formula (I) and the effect on their body weight is measured. The compounds are dosed bid at 10 mg/kg PO, with a dose-volume of 1 mL/kg or an equivalent vehicle dose (saline) for comparison. The doses are administered AM (09:00) and PM (16:00) and the body weight is measured in the morning before dosing. There are typically 8 animals per group. FIGS. 2 to 4 show the cumulative body weight change (%) observed in a 4 day study in DIO rats for Examples 7, 20 and 30, respectively.

Leptin Assay in Non-Recombinant System

Although well-characterised in recombinant systems (e.g. ObRb-transfected HEK293 cells), where leptin elicits a very marked increase in STAT3 phosphorylation, these systems have often failed to provide an accurate measure of activity of a test compound towards the leptin receptor. It seems that overexpression of the receptor (as well as the possibility for different drugs to act on different parts of the signaling pathway triggered by leptin association with its receptor) results in most cases in the absence of activity of the drugs tested.

The leptin receptor expression in non-recombinant system is often fluctuating and care must be given to identify a system where signal stability remains within experiments. Using such a system, leptin receptor antagonist mimetics could be identified by evaluating their action vs. leptin (see below).

Leptin is produced chiefly in adipose cells, but in humans, mRNA encoding leptin is also present in the placenta. Here, leptin might play an important proliferative role in the microvasculature. The possibility to use this hypothesis in a native cell line was evaluated.

JEG-3 Protocol

Figure 5:
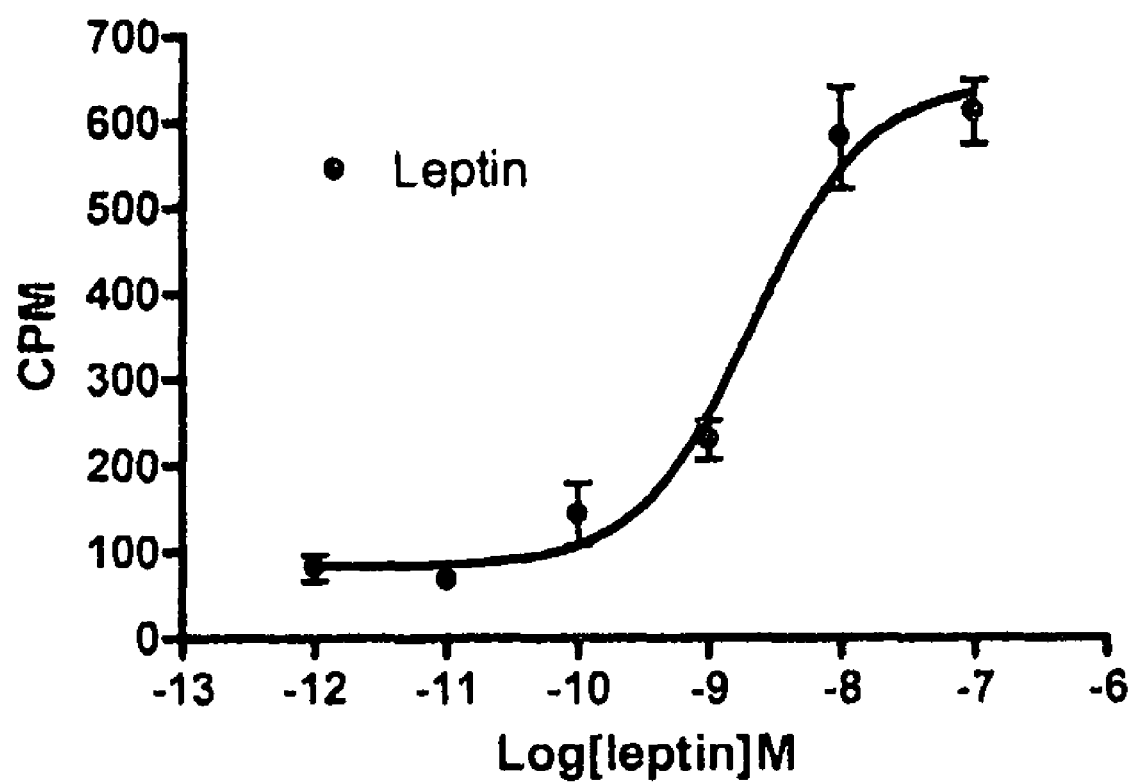
FIG. 5 shows the concentration-dependent increase in [$^3$H]-thymidine incorporation by JEG-3 cells for leptin.

In JEG-3 cells (choriocarcinoma cell line) leptin is able to stimulate proliferation up to 3 fold (Biol. Reprod. (2007) 76: 203-10). Leptin also causes a concentration-dependent increase in [$^3$H]-thymidine incorporation in JEG-3 cells (FIG. 5, maximal effect at 100 nM ($EC_{50}$=2.1 nM)). The radioactivity incorporated by the cells is an index of their proliferative activity and is measured in counts per minute (CPM) with a liquid scintillation beta counter.

This finding can be applied to test whether a compound is able to either reproduce the effect of leptin on cell proliferation (leptin receptor agonist mimetic) (i.e., a given compound will cause an increase in incorporated [$^3$H]-Thymidine by the cells) or to inhibit the effect of leptin (antagonistic effect) by preventing the leptin-mediated increase in [H]-thymidine incorporation.

This approach has the advantage of using a non-recombinant system and has reasonable reproducibility and robustness.

Measurement of Brain Penetration

The test species (rodent) is given a bolus dose of the substrate under investigation, usually via intravenous (IV) or oral (PO) routes. At appropriate time points, blood samples are taken and the resultant plasma extracted and analysed for substrate concentration and, where appropriate, metabolite concentration. At similar time points, animals from another group are sacrificed, brains isolated and the brain surface cleaned. Brain samples are then homogenised, extracted and analysed for substrate concentration and, where appropriate, metabolite concentration. Alternatively, microdialysis probes are implanted into one or more brain regions of the test species and samples collected at appropriate time points for subsequent analysis. This method has the advantage of measuring only extra-cellular substrate concentration. Plasma and brain concentrations are then compared and ratios calculated, either by comparison of averaged concentrations at individual time points, or by calculation of the area-under-the-curve (AUC) of the concentration-time plots.

The invention claimed is:

1. A compound selected from the group consisting of:
morpholin-3-ylmethyl 4-phenylpiperazine-1-carboxylate;
[(2S)-4-methylmorpholin-2-yl]methyl 4-(2,4-difluorophenyl)piperazine-1-carboxylate;
[(2R)-4-methylmorpholin-2-yl]methyl 4-(2,4-difluorophenyl)piperazine-1-carboxylate;
morpholin-2-ylmethyl 4-(4-fluorophenyl)piperazine-1-carboxylate;

(2S)-morpholin-2-ylmethyl 4-(4-fluorophenyl)piperazine-1-carboxylate;

(2R)-morpholin-2-ylmethyl 4-(4-fluorophenyl)piperazine-1-carboxylate;

morpholin-3-ylmethyl 4-(4-fluorophenyl)piperazine-1-carboxylate;

(3S)-morpholin-3-ylmethyl 4-(4-fluorophenyl)piperazine-1-carboxylate;

(3R)-morpholin-3-ylmethyl 4-(4-fluorophenyl)piperazine-1-carboxylate;

and pharmaceutically acceptable salts thereof.

2. A compound according to claim 1, the compound being morpholin-3-ylmethyl 4-phenylpiperazine-1-carboxylate, or a pharmaceutically acceptable salt thereof.

3. A compound according to claim 1, the compound being [(2S)-4-methylmorpholin-2-yl]methyl 4-(2,4-difluorophenyl)piperazine-1-carboxylate, or a pharmaceutically acceptable salt thereof.

4. A compound according to claim 1, the compound being [(2R)-4-methylmorpholin-2-yl]methyl 4-(2,4-difluorophenyl)piperazine-1-carboxylate, or a pharmaceutically acceptable salt thereof.

5. A compound according to claim 1, the compound being morpholin-2-ylmethyl 4-(4-fluorophenyl)piperazine-1-carboxylate, or a pharmaceutically acceptable salt thereof.

6. A compound according to claim 1, the compound being (2S)-morpholin-2-ylmethyl 4-(4-fluorophenyl)piperazine-1-carboxylate, or a pharmaceutically acceptable salt thereof.

7. A compound according to claim 1, the compound being (2R)-morpholin-2-ylmethyl 4-(4-fluorophenyl)piperazine-1-carboxylate, or a pharmaceutically acceptable salt thereof.

8. A compound according to claim 1, the compound being morpholin-3-ylmethyl 4-(4-fluorophenyl)piperazine-1-carboxylate, or a pharmaceutically acceptable salt thereof.

9. A compound according to claim 1, the compound being (3S)-morpholin-3-ylmethyl 4-(4-fluorophenyl)piperazine-1-carboxylate, or a pharmaceutically acceptable salt thereof.

10. A compound according to claim 1, the compound being (3R)-morpholin-3-ylmethyl 4-(4-fluorophenyl)piperazine-1-carboxylate, or a pharmaceutically acceptable salt thereof.

11. A pharmaceutical formulation comprising a compound according to claim 1 as an active ingredient, in combination with a pharmaceutically acceptable diluent or carrier.

12. A pharmaceutical formulation comprising a compound according to claim 2 as an active ingredient, in combination with a pharmaceutically acceptable diluent or carrier.

13. A pharmaceutical formulation comprising a compound according to claim 3 as an active ingredient, in combination with a pharmaceutically acceptable diluent or carrier.

14. A pharmaceutical formulation comprising a compound according to claim 4 as an active ingredient, in combination with a pharmaceutically acceptable diluent or carrier.

15. A pharmaceutical formulation comprising a compound according to claim 5 as an active ingredient, in combination with a pharmaceutically acceptable diluent or carrier.

16. A pharmaceutical formulation comprising a compound according to claim 6 as an active ingredient, in combination with a pharmaceutically acceptable diluent or carrier.

17. A pharmaceutical formulation comprising a compound according to claim 7 as an active ingredient, in combination with a pharmaceutically acceptable diluent or carrier.

18. A pharmaceutical formulation comprising a compound according to claim 8 as an active ingredient, in combination with a pharmaceutically acceptable diluent or carrier.

19. A pharmaceutical formulation comprising a compound according to claim 9 as an active ingredient, in combination with a pharmaceutically acceptable diluent or carrier.

20. A pharmaceutical formulation comprising a compound according to claim 10 as an active ingredient, in combination with a pharmaceutically acceptable diluent or carrier.

\* \* \* \* \*